US006635764B2

(12) United States Patent
Mammen et al.

(10) Patent No.: US 6,635,764 B2
(45) Date of Patent: Oct. 21, 2003

(54) THERAPEUTIC UREAS

(75) Inventors: Mathai Mammen, Redwood City, CA (US); David Oare, Belmont, CA (US)

(73) Assignee: Theravance, Inc., South San Francisco, CA (US)

( * ) Notice: Subject to any disclaimer, the term of this patent is extended or adjusted under 35 U.S.C. 154(b) by 30 days.

(21) Appl. No.: 09/732,514

(22) Filed: Dec. 7, 2000

(65) Prior Publication Data

US 2002/0049195 A1 Apr. 25, 2002

Related U.S. Application Data

(63) Continuation-in-part of application No. 09/456,170, filed on Dec. 7, 1999, now abandoned.

(51) Int. Cl.$^7$ ............... C07D 211/50; C07D 401/00; C07C 273/00; A61K 31/455; A61K 31/17
(52) U.S. Cl. ............... 546/224; 435/7.1; 435/7.2; 536/184; 536/192; 536/195; 536/207; 536/208; 536/223; 564/32; 564/48; 514/315; 514/317; 514/326; 514/329; 514/588; 514/596; 436/501
(58) Field of Search ............ 435/7.1, 7.2; 436/501; 546/184, 192, 195, 207, 208, 223, 224; 564/32, 48; 514/315, 317, 326, 329, 588, 596

(56) References Cited

U.S. PATENT DOCUMENTS

| | | | | |
|---|---|---|---|---|
| 4,567,178 A | | 1/1986 | Eberlein et al. ............ | 514/215 |
| 4,587,046 A | | 5/1986 | Goodman et al. .......... | 530/330 |
| 4,675,326 A | | 6/1987 | Amitai et al. ............... | 514/304 |
| 5,621,010 A | * | 4/1997 | Sueda et al. ................ | 514/596 |
| 5,691,323 A | | 11/1997 | Thompson et al. .......... | 514/94 |

FOREIGN PATENT DOCUMENTS

| | | | |
|---|---|---|---|
| EP | 0419397 | 3/1991 | ......... C07D/451/04 |
| EP | 0747355 | 12/1996 | ......... C07D/211/46 |
| EP | 0863141 | 9/1998 | ......... C07D/401/06 |
| EP | 0930298 | 7/1999 | ......... C07D/211/46 |
| WO | 93/20071 | 10/1993 | ......... C07D/413/12 |
| WO | 95/06635 | 3/1995 | ......... C07D/207/14 |
| WO | 98/03632 | 1/1998 | ............ C12N/5/00 |
| WO | 99/31086 | 6/1999 | ......... C07D/401/12 |

OTHER PUBLICATIONS

Barlow, R.B., et al., "A further search for selective antagonists at M2–muscarinic receptors", *Br. J. Pharmac.*, 89, pp. 837–843, (1986).

Bonner, T.I., et al., "Identification of a Family of Muscarinic Acetylcholine Receptor Genes", *Science*, 237, pp. 527–532, (Jul. 31, 1987).

Carrithers, M.D., et al., "Synthesis and characterization of bivalent peptide ligands targeted to G–protein–coupled receptors", *Chemistry & Biology*, 3 (7), pp. 537–542, (1996).

Eglen, R.M., et al., "Muscarinic Receptor Subtypes: Pharmacology and Therapeutic Potential", *DN&P*, 10(8), pp. 462–469, (Oct. 1997).

Fisher, A., "Muscarinic agonists for the treatment of Alzheimer's disease: progress and perspectives", *Exp. Opin. Invest. Drugs*, 6 (10), Investigational Drugs—Review: Central & Peripheral Nervous System, pp. 1395–1411, (1997).

Goyal, R.K., "Muscarinic Receptor Subtypes: Physiology and Clinical Implications", *The New England Journal of Medicine*, 321 (15), pp. 1022–1029, (Oct. 12, 1989).

Graul, A., et al., "Darifenacin—Agent for Irritable Bowel Syndrome Agent for Urinary Incontinence Muscarinic M3 Antagonist", *Drugs of the Future*, 21 (11), pp. 1105–1108, (1996).

Graul, A., et al., "Tolterodine—Agent for Urinary Incontinence Muscarinic Receptor Antagonist", *Drugs of the Future*, 22 (7), pp. 733–737, (1997).

Hulme, E.C., et al., "Muscarinic Receptor Subtypes", *Annu. Rev. Pharmacol. Toxicol.*, 30, pp. 633–673, (1990).

Ishihara, Y., et al., "Central Cholinergic Agents. III. Synthesis of 2–Alkoxy–2,8–diazaspiro[4,5]decane–1,3–diones as Muscarinic Agonists", *Chem. Pharm. Bull.*, 40 (5), pp. 1177–1185, (1992).

Jakubik, J., et al., "Postitive Cooperativity of Acetylcholine and Other Agonists with Allosteric Ligands on Muscarinic Acetylcholine Receptors", *Molecular Pharmacology*, 52, pp. 172–179, (1997).

Kostenis, E., et al., "Evidence for a multiple binding mode of bispyridinium–type allosteric modulators of muscarinic receptors", *European Journal of Pharmacology*, 314, pp. 385–392, (1996).

Kostenis, E., et al., "Side Chain Variations in Bispyridinium–Type Allosteric Modulators of M2–Cholinoceptors", *Life Sciences*, 56 (11/12), Abstracts No. 13, p. 1009, (1995).

LeBoulluec, K.L., et al., "Bivalent Indoles Exhibiting Serotonergic Binding Affinity", *Bioorganic & Medicinal Chemistry Letters*, 5 (2), pp. 123–126, (1995).

Martel, A.M., et al., "Revatropate—Bronchodilator Muscarinic M3 Antagonist", *Drugs of the Future*, 22 (2), pp. 135–137, (1997).

Melchiorre, C., et al., "Antimuscarinic action of methoctramine, a new cardioselective M–2 muscarinic receptor antagonist, alone and in combination with atropine and gallamine", *European Journal of Pharmacology*, 144, pp. 117–124, (1987).

(List continued on next page.)

*Primary Examiner*—Maurie Garcia Baker
(74) *Attorney, Agent, or Firm*—Jeffrey A. Hagenah; David E. Boone

(57) ABSTRACT

This invention relates to urea compounds that are muscarinic receptor antagonists and agonists, pharmaceutical compositions comprising such compounds, and methods of preparing these compounds.

13 Claims, No Drawings

OTHER PUBLICATIONS

Melchiorre, C., et al., "Polymethylene tetraamines ad muscarinic receptor probes", *TiPs, Supplement*, pp. 55–59, (Dec. 1989).

Melchiorre, C., et al., "The Design of Novel Methoctramine–Related Tetraamines as Muscarinic Receptor Subtype Selective Antagonists", *Life Sciences*, 56 (11/12), pp. 837–844, (1995).

Moser, U., et al., "Aliphatic and Hererocyclic Analogues of Arecaidine Propargyl Ester", *Arzneim–Forsch./Drug Res.*, 45 (I) Nbr. 4, pp. 449–455, (1995).

Piergentili, A., et al., "Synthesis and Muscarinic Receptors Affinity of a Series of Antagonist Bivalent Ligands", *IL Farmaco*, 49 (2), pp. 83–87, (1994).

Portoghese, P.S., "The Role of Concepts in Structure—Activity Relationships Studies of Opioid Ligands", *Journal of Medicinal Chemistry*, 35 (11), pp. 1927–1937, (1992).

Shuker, S.B., et al., "Discovering High–Affinity Ligands for Proteins: SAR by NMR", *Science*, 274, pp. 1531–1533, (Nov. 29, 1996).

Sowell, Sr., J.W., et al., "Synthesis and Cholinergic Properties of Bis[[(dimethylamino)methyl]furanyl] Analogues of Ranitidine", *J. Med. Chem.*, 35, pp. 1102–1108, (1992).

Watson, N., et al., "Actions of methoctramine, a muscarinic M2 receptor antagonist, on muscarinic and nicotinic cholinoceptors in guinea–pig airways in vivo and in vitro", *Br. J. Pharmacology*, 105, pp. 107–112, (1992).

* cited by examiner

THERAPEUTIC UREAS

CROSS-REFERENCE TO RELATED APPLICATIONS

This application is a continuation-in-part of U.S. patent application Ser. No. 09/456,170, now abandoned filed Dec. 7, 1999.

BACKGROUND OF THE INVENTION

A receptor is a biological structure with one or more binding domains that reversibly complexes with one or more ligands, where that complexation has biological consequences. Receptors can exist entirely outside the cell (extracellular receptors), within the cell membrane (but presenting sections of the receptor to the extracellular milieu and cytosol), or entirely within the cell (intracellular receptors). They may also function independently of a cell (e.g., clot formation). Receptors within the cell membrane allow a cell to communicate with the space outside of its boundaries (i.e., signaling) as well as to function in the transport of molecules and ions into and out of the cell.

A ligand is a binding partner for a specific receptor or family of receptors. A ligand may be the endogenous ligand for the receptor or alternatively may be a synthetic ligand for the receptor such as a drug, a drug candidate or a pharmacological tool.

The super family of seven transmembrane proteins (7-TMs), also called G-protein coupled receptors (GPCRs), represents one of the most significant classes of membrane bound receptors that communicate changes that occur outside of the cell's boundaries to its interior, triggering a cellular response when appropriate. The G-proteins, when activated, affect a wide range of downstream effector systems both positively and negatively (e.g., ion channels, protein kinase cascades, transcription, transmigration of adhesion proteins, and the like).

Muscarinic receptors are members of the G-protein coupled receptors that are composed of a family of five receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor subtypes in the brain and other organs has been documented (Bonner, T. I. et al., *Science* (Washington D.C.) 1987, 237, 527–532; Goyal, R. K., *J. Med.*, 1989, 321, 1022; Hulme, E. C., et al., *Annu. Rev. harmacol. Toxicol.* 1990, 30, 633; and Eglen, R. M. and Hegde, S. S., *Drug News Perspect.* 1997, 10(8), 462–469). For example, the smooth muscle is composed largely of $M_2$ and $M_3$ receptors, cardiac muscle is composed largely of $M_2$ receptors, and salivary glands are largely composed of $M_3$ receptors.

It has been established that the muscarinic receptors are involved in diseases such as chronic obstructive pulmonary disease, asthma, irritable bowel syndrome, urinary incontinence, rhinitis, spasmodic colitis, chronic cystitis, and alzheimer,s disease, senile dementia, glaucoma, schizophrenia, gastroesophogeal reflux disease, cardiac arrhythmia, and hyper salvation syndromes (Fisher, A., *Invest. Drugs*, 1997, 6(10), 1395–1411; Martel, A. M., et al., Drugs Future, 1997, 22(2), 135–137; Graul, A. and Castaner, J., Drugs Future, 1996, 21(11), 1105–1108; and Graul, A., et al., Drugs Future, 1997, 22(7), 733–737).

A number of compounds having muscarinic receptor antagonistic activities are being used to treat these diseases. For example, oxybutynin is being used for the treatment of urinary urge incontinence and dicyclorine is being used for the treatment of irritable bowel syndrome. However, these drugs have limited utility as they produce side effects such as dry mouth, blurred vision, and mydriasis.

There is currently a need for novel muscarinic receptor antagonists.

SUMMARY OF THE INVENTION

The invention is directed to urea derivatives that are muscarinic receptor antagonists and agonists and that are useful in the treatment and prevention of diseases mediated by muscarinic receptors (e.g. chronic obstructive pulmonary disease, chronic bronchitis, irritable bowel syndrome, urinary incontinence, and the like).

Accordingly, the invention provides a compound of the invention which is a compound of Formula (I):

wherein:

$L_1$ is a group of formula (a):

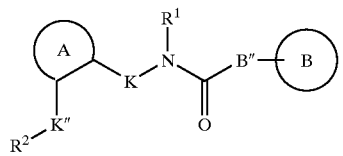

wherein:

A is an aryl or a heteroaryl ring;

B" is —$NR^{a-}$ wherein $R^a$ is hydrogen, alkyl, aryl, heteroaryl, or substituted alkyl;

$R^1$ is hydrogen or alkyl;

$R^2$ is Het, or is selected from a group consisting of formula (i), (ii), and (iii):

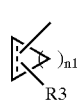

(i)

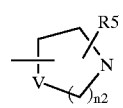

(ii)

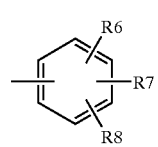

(iii)

wherein:
—— is an optional double bond;
$n_1$ is an integer of from 1 to 4;
$n_2$ is an integer of from 1 to 3;
V is —CH—, —O—, —S(O)$n_3$— (where $n_3$ is an integer of from 0 to 2), or —$NR^4$— (wherein $R^4$ is hydrogen, alkyl, substituted alkyl, aryl, or heteroaryl);
"Het" is a heteroaryl ring which optionally attaches (a) to a linker;
$R^3$ is hydrogen, alkyl, amino, substituted amino, —$OR^a$ (where $R^a$ is hydrogen, alkyl, or acyl), or a covalent bond attaching (a) to a linker;

R⁵ is hydrogen, alkyl, amino, substituted amino, —OR$^b$ (where R$^b$ is hydrogen or alkyl), aryl, aralkyl, heteroaralkyl, or a covalent bond attaching (a) to a linker;

R⁶, R⁷, and R⁸ are, independently of each other, hydrogen, halo, hydroxy, alkoxy, haloalkoxy, carboxy, alkoxycarbonyl, alkyl optionally substituted with one, two or three substituents selected from halo, hydroxy, carboxy, alkoxycarbonyl, alkylthio, alkylsulfonyl, amino, substituted amino, or a covalent bond attaching (a) to a linker;

K is a bond or an alkylene group;

K" is a bond, —C(O)—, —S(O)$_{n4}$— (where $n_4$ is an integer of from 0 to 2), or an alkylene group optionally substituted with a hydroxyl group; and B is heterocycloamino or heteroarylamino, which optionally attaches (a) to a linker;

provided that at least one of the R⁵, R⁶, R⁷, R⁸, "Het", heterocycloamino or heteroarylamino groups attaches (a) to a linker;

X is a linker;

L$_2$ is a group selected from a group consisting of:
(i) a group of formula (b):

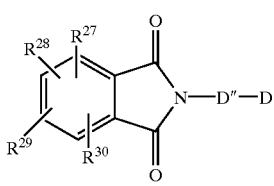

(b)

wherein:

D" is alkylene;

D is —NR³¹R³², —N⁺(R³³R³⁴R³⁵) or —OR³² where R³¹, R³³, and R³⁴ are, independently of each other, hydrogen, alkyl, or aralkyl; and R³² and R³⁵ represent a covalent bond attaching (b) to a linker;

R²⁷ is hydrogen, halo, nitro, cyano, hydroxy, alkoxy, carboxy, alkoxycarbonyl, acyl, thio, alkylthio, alkylsulfonyl, alkylsulfinyl, sulfonamido, alkylsulfonamido, carbamoyl, thiocarbamoyl, mono or dialkylcarbamoyl, amino, mono- or dialkylamino, aryl, aryloxy, arylthio, heteroaryl, hetaryloxy, heteroarylthio, heterocyclyl, heterocyclyloxy, aralkyl, heteroaralkyl, or alkyl optionally substituted with one, two or three substituents selected from halo, hydroxy, carboxy, alkoxycarbonyl, alkylthio, alkylsulfonyl, amino, or substituted amino;

R²⁸ is hydrogen, halo, nitro, cyano, hydroxy, alkoxy, carboxy, alkoxycarbonyl, acyl, thio, alkylthio, alkylsulfonyl, alkylsulfinyl, sulfonamido, alkylsulfonamido, carbamoyl, thiocarbamoyl, mono or dialkylcarbamoyl, amino, mono- or dialkylamino, or alkyl optionally substituted with one, two, or three substituents selected from halo, hydroxy, carboxy, alkoxycarbonyl, alkylthio, alkylsulfonyl, amino, or substituted amino;

R²⁹ and R³⁰ are, independently of each other, hydrogen, alkyl, haloalkyl, halo, nitro, cyano, hydroxy, alkoxy, alkoxycarbonyl, acyl, thio, alkylthio, amino, mono- or dialkylamino; or one of R²⁷, R²⁸, R²⁹, or R³⁰ together with the adjacent group forms a methylenedioxy or ethylenedioxy group;

(ii) a group of formula (c):

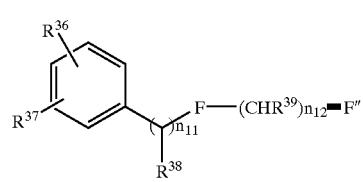

(c)

wherein:

$n_{11}$ is an integer of from 1 to 7;

$n_{12}$ is 0 to 7;

F is —NR⁴⁰—, —O—, —S—, or —CHR⁴¹— (wherein R⁴⁰ and R⁴¹ are, independently of each other, hydrogen, alkyl, or substituted alkyl);

F" is a covalent bond, —OR⁴³, —NR⁴²R⁴³, or —N⁺R⁴³R⁴⁴R⁴⁵ wherein R⁴² is hydrogen or alkyl, R⁴⁴ and R⁴⁵ are alkyl, and R⁴³ is hydrogen, alkyl, or a covalent bond attaching (c) to a linker;

R³⁶ is hydrogen, alkyl, halo, nitro, cyano, hydroxy, alkoxy, carboxy, alkoxycarbonyl, acyl, thio, alkylthio, alkylsulfonyl, alkylsulfinyl, sulfonamido, alkylsulfonamido, carbamoyl, thiocarbamoyl, mono or dialkylcarbamoyl, amino, mono- or dialkylamino, aryl, aryloxy, arylthio, heteroaryl, hetaryloxy, heteroarylthio, heterocyclyl, heterocyclyloxy, aralkyl, heteroaralkyl, or alkyl optionally substituted with one, two or three substituents selected from halo, hydroxy, carboxy, alkoxycarbonyl, alkylthio, alkylsulfonyl, amino, or substituted amino;

R³⁷ is hydrogen, alkyl, halo, nitro, cyano, hydroxy, alkoxy, alkoxycarbonyl, acyl, thio, alkylthio, amino, mono- or dialkylamino, aryl, aryloxy, arylthio, heteroaryl, hetaryloxy, heteroarylthio, heterocyclyl, heterocyclyloxy, aralkyl, heteroaralkyl, or alkyl optionally substituted with one, two or three substituents selected from halo, hydroxy, carboxy, alkoxycarbonyl, alkylthio, alkylsulfonyl, amino, or substituted amino; and R³⁸ is hydrogen, alkyl, halo, hydroxy, alkoxy, or a covalent bond attaching the ligand to a linker provided that at least one of R³⁸ and R⁴³ attaches (c) to a linker;

R³⁹ is hydrogen, alkyl, halo, hydroxy, alkoxy, or substituted alkyl; and (iii) a group of formula (d) or (e):

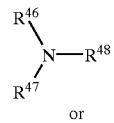

(d)

or

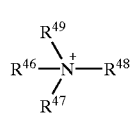

(e)

wherein:

R⁴⁶ is alkyl, substituted alkyl, cycloalkyl, substituted cycloalkyl, or heterocycle;

R⁴⁷ is alkyl, substituted alkyl, aryl, acyl, heterocycle, or —COOR⁵⁰ where R⁵⁰ is alkyl; or R⁴⁶ and R⁴⁷ together with the nitrogen atom to which they are attached form heterocycle, which heterocycle, in addition to optionally bearing the optional substituents defined hereinbelow for a heterocycle, can also optionally be substituted with one or more (e.g. 1, 2, 3, or 4) alkyl, substituted alkyl, alkenyl, substituted alkenyl, alkynyl, or substituted alkynyl.

R⁴⁸ is a covalent bond that attaches the (d) or the (e) to a linker; and

R⁴⁹ is alkyl;

or a pharmaceutically acceptable salt; or prodrug thereof.

Preferably X is a group of formula:

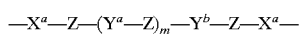

wherein m is an integer of from 0 to 20;

Xᵃ at each separate occurrence is selected from the group consisting of —O—, —S—, —NR—, —C(O)—, —C(O)O—, —C(O)NR—, —C(S)—, —C(S)O—, —C(S)NR— or a covalent bond where R is as defined below;

Z at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;

Yᵃ and Yᵇ at each separate occurrence are selected from the group consisting of —O—, —C(O)—, —OC(O)—, —C(O)O—, —NR—, —S(O)n—, —C(O)NR'—, —NR'C(O)—, —NR'C(O)NR'—, —NR'C(S)NR'—, —C(—NR')—NR'—, —NR'—C(—NR')—, —OC(O)—NR'—, —NR'—C(O)—O—, —N—C(R")—NR'—, —NR'—C(R")—N—, —P(O)(OR')—O—, —O—P(O)(OR'), S(O)ₙCR'R"—, —S(O)ₙ—, —NR'—, —NR'—S(O)ₙ—, —S—S—, and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic (preferably, at least one of Xᵃ, Yᵃ, Yᵇ or Z is not a covalent bond).

The invention also provides a compound of the invention which is a compound of formula (IV):

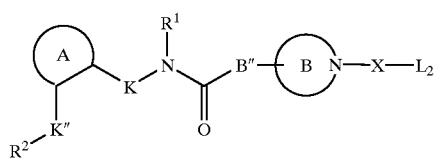

wherein R², K", A, K, R¹, B", B, X, and L₂ have any of the values defined herein; or a pharmaceutically acceptable salt; or prodrug thereof. A preferred compound of the invention is a compound of formula (IVa):

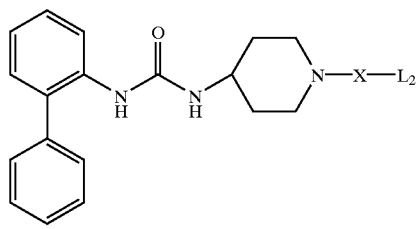

wherein X, and L₂ have any of the values defined herein; or a pharmaceutically acceptable salt; or prodrug thereof.

The invention also provides a pharmaceutical composition comprising a pharmaceutically acceptable carrier and a compound of the invention or a pharmaceutically acceptable salt or prodrug thereof.

The invention also provides synthetic intermediates disclosed herein, as well as synthetic methods useful for preparing such intermediates, and synthetic methods useful for preparing compounds of the invention or salts thereof.

The invention also provides a method of treating diseases mediated by a muscarinic receptor in a mammal, comprising administering to said mammal a therapeutically effective amount of a compound of the invention or a pharmaceutically acceptable salt or prodrug thereof.

The invention also provides a compound of the invention or a pharmaceutically acceptable salt or prodrug thereof for use in medical therapy, as well as the use of a compound of Formula (I) or a pharmaceutically acceptable salt or prodrug thereof in the preparation of a medicament for the treatment of a disease mediated by a muscarinic receptor in a mammal.

Applicant has discovered that urea compounds of the present invention are metabolically more stable than compounds lacking such a urea functionality. Accordingly, compounds of the present invention have longer metabolic half-lives and/or longer duration of action in vivo, which can reduce the dose required for administration or can reduce the likelihood of the generation of unwanted metabolites.

DETAILED DESCRIPTION OF THE INVENTION

The following terms have the following meanings unless otherwise indicated. Any undefined terms have their art recognized meanings.

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above wherein one or more carbon atoms in the alkyl chain have been optionally replaced with a heteroatom such as —O—, —S(O)n— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ may be the same or different and and are chosen from hydrogen, optionally substituted alkyl, cycloalkyl, alkenyl, cycloalkenyl, alkynyl, aryl, heteroaryl and heterocyclic. This term is exemplified by groups such as hydroxymethyl, hydroxyethyl, hydroxypropyl, 2-aminoethyl, 3-aminopropyl, 2-methylaminoethyl, 3-dimethylaminopropyl, 2-sulfonamidoethyl, 2-carboxyethyl, and the like.

The term "alkylene" refers to a diradical of a branched or unbranched saturated hydrocarbon chain, preferably having from 1 to 40 carbon atoms, more preferably 1 to 10 carbon atoms and even more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkylaminoalkyl", "alkylaminoalkenyl" and "alkylaminoalkynyl" refers to the groups R$^a$NHR$^b$— where R$^a$ is alkyl group as defined above and R$^b$ is alkylene, alkenylene or alkynylene group as defined above. Such groups are exemplified by 3-methylaminobutyl, 4-ethylamino-1,1-dimethylbutyn-1-yl, 4-ethylaminobutyn-1-yl, and the like.

The term "alkaryl" or "aralkyl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "alkylalkoxy" refers to the groups -alkylene-O-alkyl, alkylene-O-substituted alkyl, substituted alkylene-O-alkyl, and substituted alkylene-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$), and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$), and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH=CH—), the propenylene isomers (e.g., —CH$_2$CH=CH— or —C(CH$_3$)=CH—), and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1–6 sites of acetylene (triple bond) unsaturation. Preferred alkynyl groups include ethynyl (—C≡CH), propargyl (—CH$_2$C≡CH), and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

The term "alkynylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups include ethynylene (—C≡C—), propargylene (—CH$_2$C≡C—), and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl, and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl, and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl, and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl, and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Preferred aryls include phenyl, naphthyl and the like. Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclic provided that both R's are not hydrogen.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl, and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring). Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "heteroaralkyl" refers to the groups -alkylene-heteroaryl where alkylene and heteroaryl are defined herein. Such heteroaralkyl groups are exemplified by pyridylmethyl, pyridylethyl, indolylmethyl, and the like.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl, and the like.

The term "heterocycle" or "heterocyclic" or refers to a monoradical saturated unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring. Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Examples of nitrogen heteroaryls and heterocycles include, but are not limited to, pyrrole, thiophene, furan, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, pyrrolidine, piperidine, piperazine, indoline, morpholine, tetrahydrofuranyl, tetrahydrothiophene, and the like as well as N-alkoxy-nitrogen containing heterocycles.

The term "heterocyclooxy" refers to the group heterocyclic-O—.

The term "thioheterocyclooxy" refers to the group heterocyclic-S—.

The term "heterocyclene" refers to the diradical group formed from a heterocycle, as defined herein, and is exemplified by the groups 2,6-morpholino, 2,5-morpholino and the like.

"Heteroarylamino" means a 5 membered aromatic ring wherein one or two ring atoms are N, the remaining ring atoms being C. The heterocycloamino ring may be fused to a cycloalkyl, aryl or heteroaryl ring, and it may be optionally substituted with one or more substituents, preferably one or two substituents, selected from alkyl, substituted alkyl, cycloalkyl, aryl, aralkyl, heteroaryl, heteroaralkyl, halo, cyano, acyl, amino, substituted amino, acylamino, —OR (where R is hydrogen, alkyl, alkenyl, cycloalkyl, acyl, aryl, heteroaryl, aralkyl, or heteroaralkyl), or —S(O)nR [where n is an integer from 0 to 2 and R is hydrogen (provided that n is 0), alkyl, alkenyl, cycloalkyl, amino, heterocyclo, aryl, heteroaryl, aralkyl, or heteroaralkyl]. More specifically the term heterocycloamino includes, but is not limited to, imidazole, pyrazole, benzimidazole and benzpyrazole.

"Heterocycloamino" means a saturated monovalent cyclic group of 4 to 8 ring atoms, wherein at least one ring atom is N and optionally contains one or two additional ring heteroatoms selected from the group consisting of N, O, or S(O)n (where n is an integer from 0 to 2), the remaining ring atoms being C, where one or two C atoms may optionally be replaced by a carbonyl group. The heterocycloamino ring may be fused to a cycloalkyl, aryl or heteroaryl ring, and it may be optionally substituted with one or more substituents, preferably one or two substituents, selected from alkyl, substituted alkyl, cycloalkyl, aryl, aralkyl, heteroaryl, heteroaralkyl, halo, cyano, acyl, amino, substituted amino, acylamino, —OR (where R is hydrogen, alkyl, alkenyl, cycloalkyl, acyl, aryl, heteroaryl, aralkyl, or heteroaralkyl), or —S(O)nR [where n is an integer from 0 to 2 and R is hydrogen (provided that n is 0), alkyl, alkenyl, cycloalkyl, amino, heterocyclo, aryl, heteroaryl, aralkyl, or heteroaralkyl]. More specifically the term heterocycloamino includes, but is not limited to, pyrrolidino, piperidino, morpholino, piperazino, indolino, or thiomorpholino. The term heterocycloamino also includes, quinuclidine, 1-azabicyclo[2.2.1]heptyl, 1-azabicyclo[3.2.1]octyl and the derivatives thereof.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "spiro-attached cycloalkyl group" refers to a cycloalkyl group attached to another ring via one carbon atom common to both rings.

The term "thiol" refers to the group —SH.

The term "thioalkoxy" or "alkylthio" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

Unless specified otherwise, all ranges referred to herein include the stated end-point values.

The term "pharmaceutically-acceptable salt" refers to salts which retain biological effectiveness and are not biologically or otherwise undesirable. In many cases, the compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri (cycloalkyl) amines, substituted cycloalkyl amines, disubstituted cycloalkyl amine, trisubstituted cycloalkyl amines, cycloalkenyl amines, di(cycloalkenyl) amines, tri (cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(isopropyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

The term "protecting group" or "blocking group" refers to any group which when bound to one or more hydroxyl, thiol, amino or carboxyl groups of the compounds (including intermediates thereof) prevents reactions from occurring at these groups and which protecting group can be removed by conventional chemical or enzymatic steps to reestablish the hydroxyl, thiol, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Preferred removable thiol blocking groups include disulfide groups, acyl groups, benzyl groups, and the like. Preferred removable amino blocking groups include conventional substituents such as t-butyoxycarbonyl (t-BOC), benzyloxycarbonyl (CBZ), fluorenylmethoxy-carbonyl (FMOC), allyloxycarbonyl (ALOC), and the like which can be removed by conventional conditions compatible with the nature of the product. Preferred carboxyl protecting groups include esters such as methyl, ethyl, propyl, t-butyl etc. which can be removed by mild conditions compatible with the nature of the product.

The term "optional" or "optionally" means that the subsequently described event, circumstance or substituent may or may not occur, and that the description includes instances where said event or circumstance occurs and instances where it does not.

The term "inert organic solvent" or "inert organic solvent" means a solvent which is inert under the conditions of the reaction being described in conjunction therewith including, by way of example only, benzene, toluene, acetonitrile, tetrahydrofuran, dimethylformamide, chloroform, methylene chloride, diethyl ether, ethyl acetate, acetone, methylethyl ketone, methanol, ethanol, propanol, isopropanol, t-butanol, dioxane, pyridine, and the like. Unless specified to the contrary, the solvents used in the reactions described herein are inert solvents.

The term "treatment" refers to any treatment of a pathologic condition in a mammal, particularly a human, and includes:

(i) preventing the pathologic condition from occurring in a subject which may be predisposed to the condition but has not yet been diagnosed with the condition and, accordingly, the treatment constitutes prophylactic treatment for the disease condition;

(ii) inhibiting the pathologic condition, i.e., arresting its development;

(iii) relieving the pathologic condition, i.e., causing regression of the pathologic condition; or (iv) relieving the conditions mediated by the pathologic condition.

The term "pathologic condition which is modulated by treatment with a ligand" covers all disease states (i.e., pathologic conditions) which are generally acknowledged in the art to be usefully treated with a ligand for the muscarinic receptors in general, and those disease states which have been found to be usefully treated by a compound of the invention. Such disease states include, by way of example only, the treatment of a mammal afflicted with chronic obstructive pulmonary disease, chronic bronchitis, irritable bowel syndrome, urinary incontinence, and the like.

The term "therapeutically effective amount" refers to that amount of a compound which is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "linker", identified by the symbol 'X' refers to a group or groups that covalently attaches $L_1$ and $L_2$. Additionally, the linker can be either a chiral or achiral molecule. The term "linker" does not, however, extend to cover solid inert supports such as beads, glass particles, fibers, and the like. But it is understood that the compounds of this invention can be attached to a solid support if desired. For example, such attachment to solid supports can be made for use in separation and purification processes and similar applications.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

While the broadest definition of this invention is set forth in the Summary of the Invention, certain compounds of Formula (I) may be preferred. Specific and preferred values listed herein for radicals, substituents, and ranges, are for illustration only; they do not exclude other defined values or other values within defined ranges for the radicals and substituents A preferred value for A is phenyl or pyridine A preferred value for $R^1$ is hydrogen methyl, or ethyl.

Another preferred value for $R^1$ is hydrogen.

A preferred value for $R^2$ is pyrrolyl, pyridinyl, or imidazolyl.

Another preferred value for $R^2$ is phenyl.

A preferred value for V is —CH— or —$NR^4$— (wherein $R^4$ is hydrogen, alkyl, substituted alkyl, aryl, or heteroaryl).

A preferred value for $R^3$ is hydrogen or alkyl

A preferred value for $R^5$ is hydrogen, alkyl, aryl, aralkyl, heteroaralkyl, or a covalent bond attaching (a) to a linker Another preferred value for $R^5$ is hydrogen, methyl, phenyl optionally substituted with alkyl, alkoxy, halo, hydroxy, carboxy, or amino, benzyl optionally substituted with alkyl, alkoxy, halo, hydroxy, carboxy, or amino.

A preferred value for $R^6$, $R^7$, and $R^8$ independent of each other is hydrogen, alkyl, nitro, hydroxy, or amino.

A preferred value for K is alkylene having from 1 to 10 carbon atoms.

A preferred value for K is alkylene having from 1 to 5 carbon atoms.

A preferred value for K is a bond or a methylene group.

A preferred value for K" is a bond.

A preferred value for $R_a$ is hydrogen.

A preferred value for B is a heterocycloamino group which attaches (a) to a linker.

Another preferred value for B is a formula selected from a group consisting of formula (j), formula (k), and formula (l):

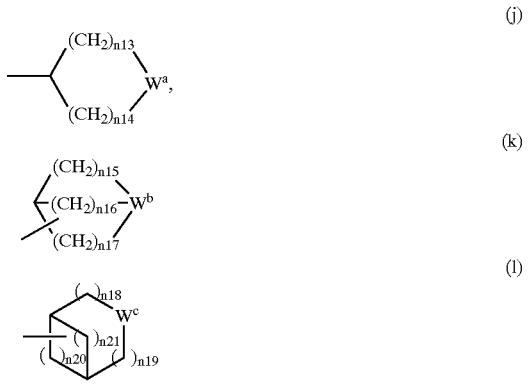

wherein:

$n_{13}$ and $n_{14}$ are, independently of each other, an integer of from 0 to 4 provided that $n_{13}+n_{14}$ is an integer of from 3 to 5;

$n_{15}$ and $n_{17}$ are, independently of each other, an integer of from 0 to 4 provided that $n_{15}+n_{17}$ is an integer of from 3 to 5;

$n_{16}$ is an integer of from 0 to 3 provided that $n_{15}+n_{16}$ is an integer of from 3 to 5;

$n_{18}$, $n_{19}$ and $n_{20}$ are, independently of each other, an integer of from 0 to 3 provided that $n_{18}+n_{19}+n_{20}$ is 2 or 3;

$n_{21}$ is an integer of from 1 to 3;

$W^a$ and $W^c$ are, independently of each other:

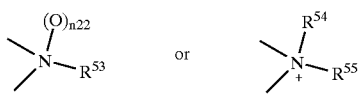

where:

$n_{22}$ is 0 or 1;

$R^{53}$ and $R^{54}$ are, independently of each other, hydrogen, alkyl, alkenyl, alkynyl, cycloalkylalkyl, aralkyl, or heterocyclylalkyl or a covalent bond attaching (a) to a linker;

$R^{55}$ is alkyl, alkenyl or alkynyl; and $W^b$ is —N(O)$n_{23}$ or —N$^+$—R$^{56}$ where $n_{23}$ is 0 or 1, and $R^{56}$ is alkyl, alkenyl, alkynyl, or aralkyl, or a covalent bond attaching (a) to a linker;

provided that a carbon other than a bridge head carbon is bonded to B".

Another preferred value for B is a ring represented by the following general formulae:

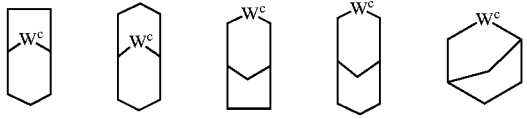

wherein a carbon atom other than a bridge head carbon is bound to B"; and $W^c$ is as defined above.

A more preferred value for B is pyrrolidine, piperidine, or hexahydroazepine attaching (a) to a linker.

Another more preferred value for B is piperidine wherein the nitrogen atom of said piperidine attaches (a) to a linker.

Another more preferred value for B is piperidin-4-yl wherein the nitrogen at the 1 position optionally attaches (a) to a linker.

Another more preferred value for B is quinuclidine, 1-azabicyclo[2.2.1]-heptyl, or 1-azabicyclo[3.2.1]octyl attaching (a) to a linker, wherein a carbon other than a bridge head carbon is bound to B".

A preferred value for D" is —(CH$_2$)$n_{43}$— where $n_{43}$ is an integer of from 1–10, preferably 2–8, more preferably 2–4. Another preferred value for $n_{43}$ is an integer of from 3–10.

A preferred value for D is —NR$^{31}$R$^{32}$ or —N$^+$(R$^{33}$R$^{34}$R$^{35}$)M$^-$ where $R^{31}$, $R^{33}$, and $R^{34}$ are, independently of each other, hydrogen or methyl, and $R^{32}$ and $R^{35}$ represent a covalent bond attaching (b) to a linker. More preferably $R^{31}$, $R^{33}$, and $R^{34}$ methyl, and $R^{32}$ and $R^{35}$ represent a covalent bond attaching (b) to a linker.

A preferred value for $R^{27}$ is hydrogen.

A preferred value for $R^{28}$ is hydrogen.

A preferred value for $R^{29}$ and $R^{30}$ independently is hydrogen; or one of $R^{27}$, $R^{28}$, $R^{29}$, or $R^{30}$ together with the adjacent group forms a methylenedioxy or ethylenedioxy group.

A preferred value for $n_{11}$ is 1.

A preferred value for $n_{12}$ is 6.

A preferred value for F is —O—.

A preferred value for F" is a covalent bond, —OR$^{43}$, —NR$^{42}$R$^{43}$ wherein $R^{42}$ is hydrogen or alkyl, or —N$^+$(R$^{43}$R$^{44}$R$^{45}$) wherein $R^{44}$ and $R^{45}$ are alkyl, and $R^{43}$ is a covalent bond attaching (c) to a linker.

A preferred value for F" is —O—, —NH—, N(CH$_3$)— or —N(CH$_3$)$_2$—

A more preferred value for F" is —NH—, N(CH$_3$)— or —N(CH$_3$)$_2$— wherein the nitrogen atom attaches (c) to a linker.

A preferred value for $R^{36}$ is hydrogen.

Preferably $R^{37}$ is ortho to the —(CHR$^{38}$)— group and is hydrogen or alkoxy. More preferably $R^{37}$ is ortho to the —(CHR$^{38}$) group and is methoxy.

Preferably is $R^3$ is hydrogen.

Preferably $R^{39}$ is hydrogen.

Preferably $L_2$ is a group of formula (d) wherein: $R^{46}$ is alkyl or substituted alkyl; $R^{47}$ is alkyl, substituted alkyl, or heterocycle; or $R^{46}$ and $R^{47}$ together with the nitrogen atom to which they are attached form heterocycle.

Preferably, $L_2$ is a group of formula A1-A241 as shown in the following table. $L_2$ is preferably linked to X through a non-aromatic nitrogen atom (e.g. a secondary amino nitrogen) of $L_2$.

| No. | $L_2$ |
|---|---|
| A1 |  |
| A2 |  |
| A3 |  |
| A4 |  |
| A5 |  |
| A6 |  |
| A7 |  |
| A8 |  |

-continued
| No. | L₂ |
|---|---|
| A9 | 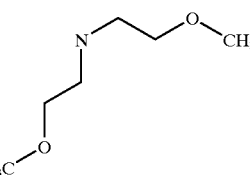 |
| A10 | 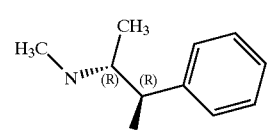 |
| A11 | 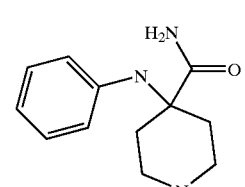 |
| A12 | 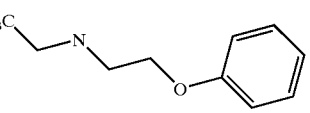 |
| A13 | 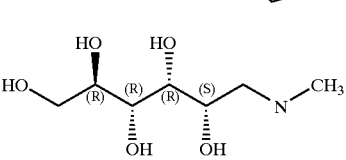 |
| A14 | 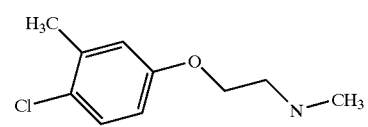 |
| A15 | 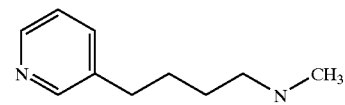 |
| A16 | 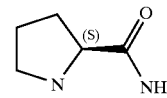 |
| A17 | 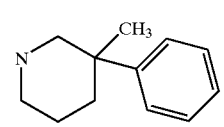 |
| A18 | 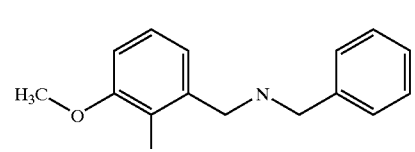 |
| A19 | 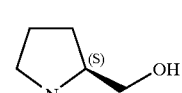 |
-continued
| No. | L₂ |
|---|---|
| A20 | 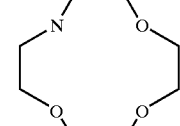 |
| A21 | 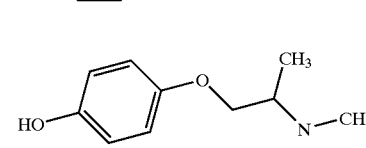 |
| A22 | 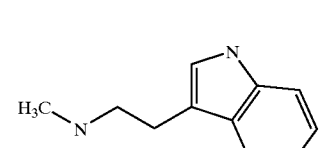 |
| A23 | 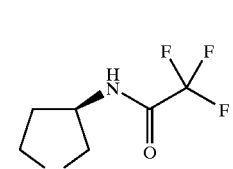 |
| A24 | 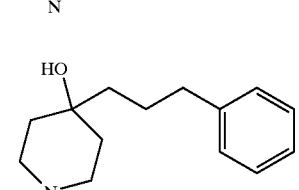 |
| A25 | 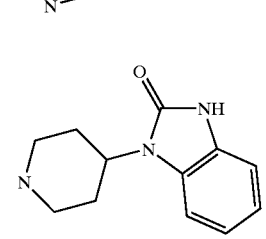 |
| A26 | 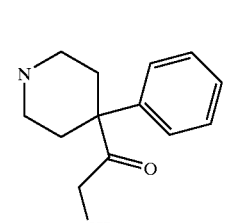 |
| A27 | 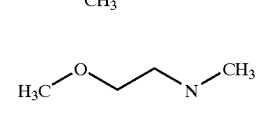 |
| A28 | 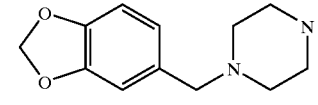 |

-continued
| No. | L₂ |
|---|---|
| A29 | 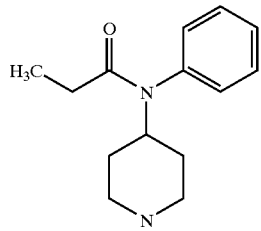 |
| A30 | 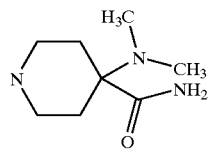 |
| A31 | 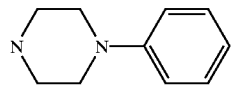 |
| A32 | 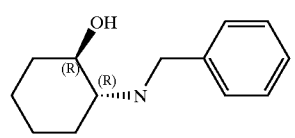 |
| A33 | 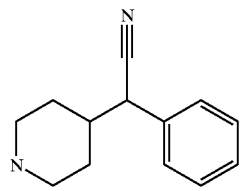 |
| A34 | 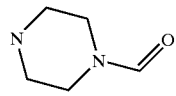 |
| A35 | 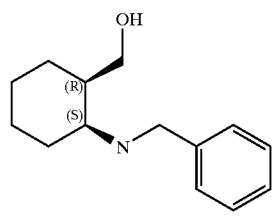 |
| A36 | 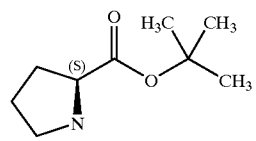 |
| A37 | 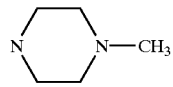 |
-continued
| No. | L₂ |
|---|---|
| A38 | 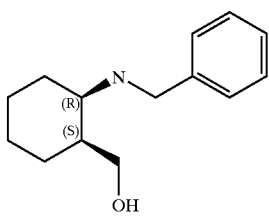 |
| A39 | 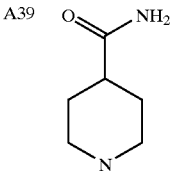 |
| A40 | 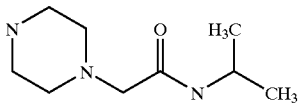 |
| A41 | 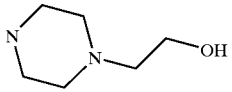 |
| A42 | 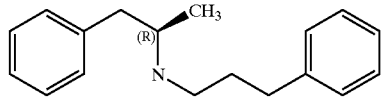 |
| A43 | 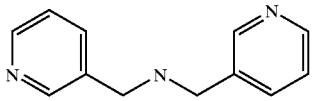 |
| A44 | 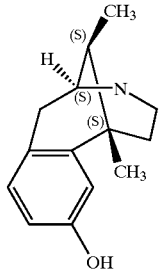 |
| A45 | 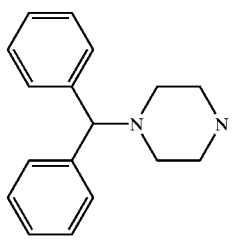 |
| A46 | 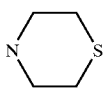 |

-continued
| No. | L₂ |
|---|---|
| A47 | 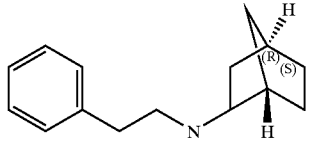 |
| A48 | 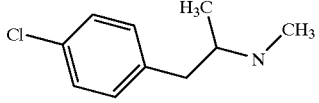 |
| A49 | 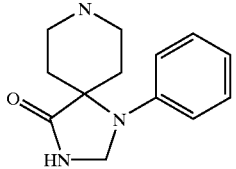 |
| A50 | 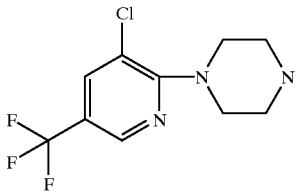 |
| A51 | 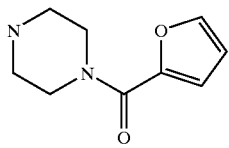 |
| A52 |  |
| A53 | 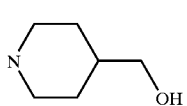 |
| A54 | 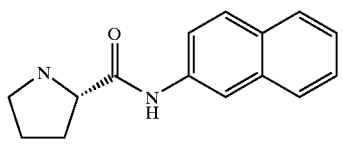 |
| A55 | 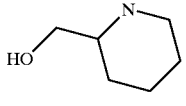 |
| A56 | 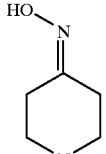 |
| A57 |  |
-continued
| No. | L₂ |
|---|---|
| A58 | 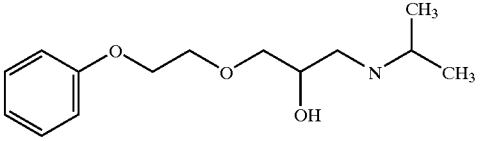 |
| A59 | 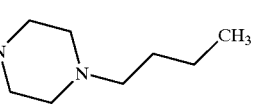 |
| A60 | 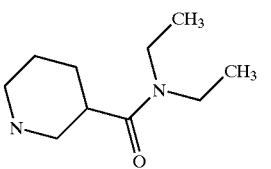 |
| A61 | 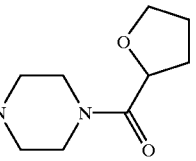 |
| A62 | 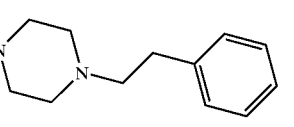 |
| A63 | 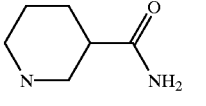 |
| A64 | 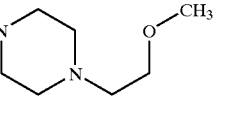 |
| A65 | 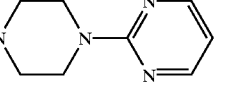 |
| A66 | 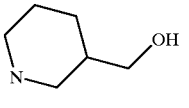 |
| A67 | 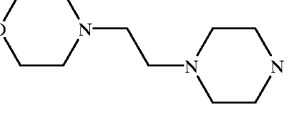 |
| A68 | 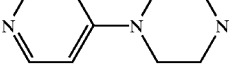 |
| A69 | 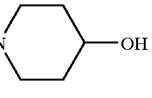 |

-continued
| No. | L₂ |
|-----|-----|
| A70 | 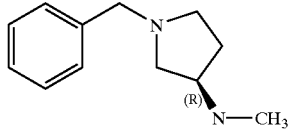 |
| A71 | 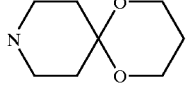 |
| A72 | 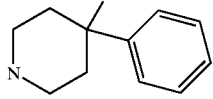 |
| A73 | 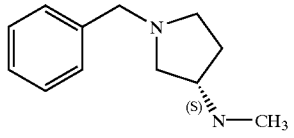 |
| A74 | 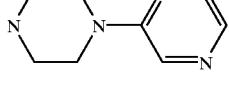 |
| A75 | 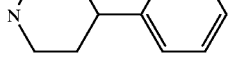 |
| A76 | 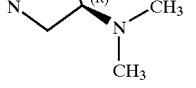 |
| A77 | 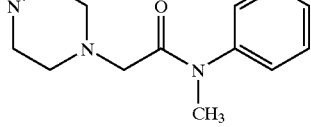 |
| A78 | 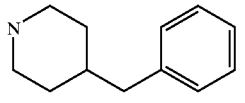 |
| A79 | 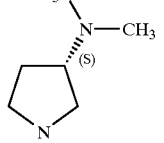 |
| A80 | 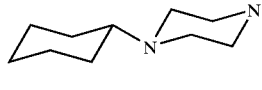 |
| A81 | 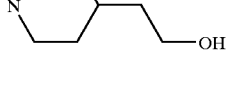 |
-continued
| No. | L₂ |
|-----|-----|
| A82 | 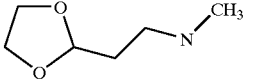 |
| A83 | 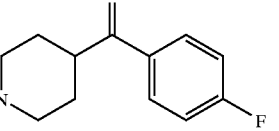 |
| A84 | 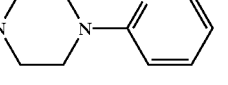 |
| A85 | 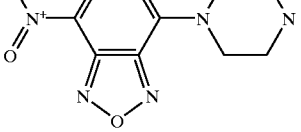 |
| A86 | 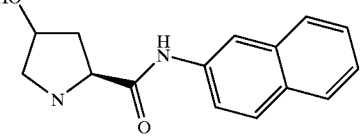 |
| A87 | 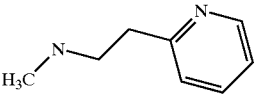 |
| A88 |  |
| A89 | 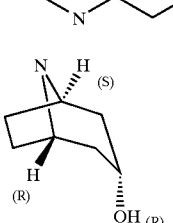 |
| A90 | 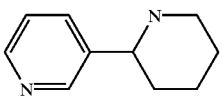 |
| A91 |  |
| A92 | 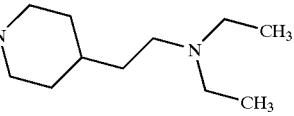 |

-continued
| No. | L₂ |
|---|---|
| A93 | 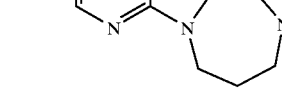 |
| A94 |  |
| A95 | 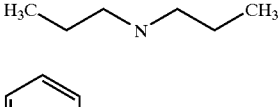 |
| A96 | 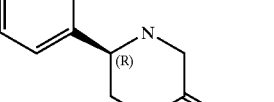 |
| A97 | 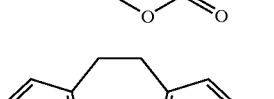 |
| A98 | 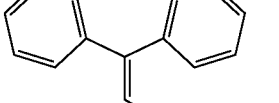 |
| A99 | 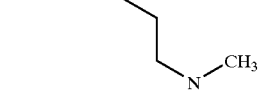 |
| A100 | 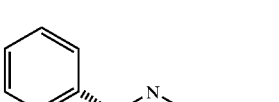 |
| A101 | 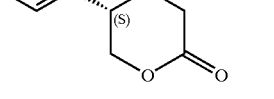 |
| A102 | 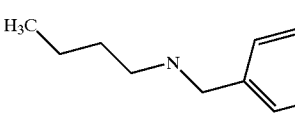 |
| A103 | |
-continued
| No. | L₂ |
|---|---|
| A104 | |
| A105 | |
| A106 | |
| A107 | |
| A108 | |
| A109 | |
| A110 | |
| A111 | |
| A112 | |
| A113 | |

-continued
| No. | L₂ |
|---|---|
| A114 | 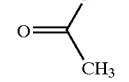 |
| A115 | |
| A116 | |
| A117 | |
| A118 | |
| A119 | |
| A120 | |
| A121 | |
| A122 | |
-continued
| No. | L₂ |
|---|---|
| A123 | 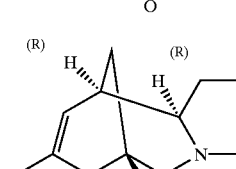 |
| A124 | |
| A125 | |
| A126 | |
| A127 | |
| A128 | |
| A129 | |
| A130 | |
| A131 | |
| A132 | |

-continued
| No. | L₂ |
|---|---|
| A133 | 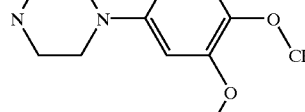 |
| A134 | 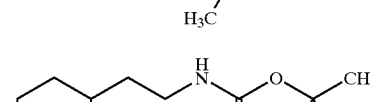 |
| A135 |  |
| A136 | 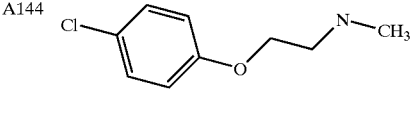 |
| A137 |  |
| A138 |  |
| A139 | 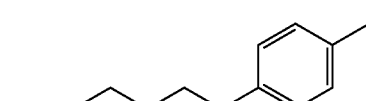 |
| A140 | 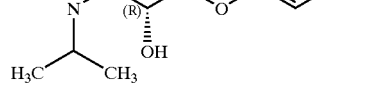 |
| A141 | 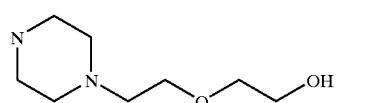 |
-continued
| No. | L₂ |
|---|---|
| A142 | |
| A143 | |
| A144 | |
| A145 | |
| A146 | |
| A147 | |
| A148 | |
| A149 | |
| A150 | |
| A151 | |
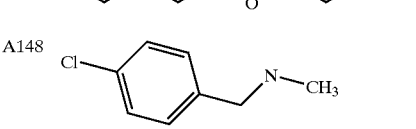

-continued
| No. | L₂ |
|---|---|
| A152 | 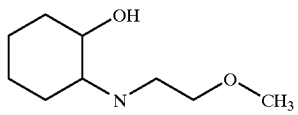 |
| A153 | 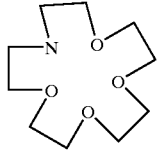 |
| A154 | 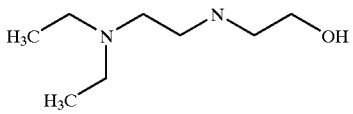 |
| A155 | 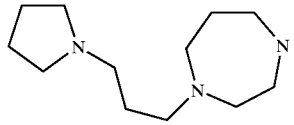 |
| A156 | 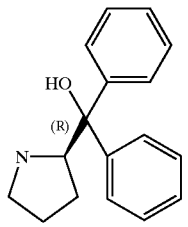 |
| A157 | 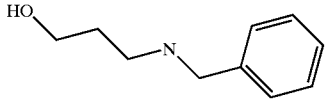 |
| A158 | 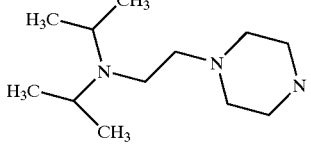 |
| A159 | 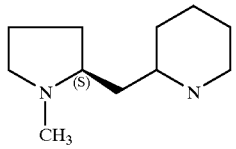 |
| A160 | 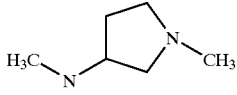 |
| A161 | 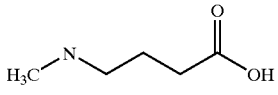 |
-continued
| No. | L₂ |
|---|---|
| A162 | 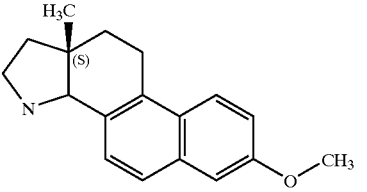 |
| A163 | 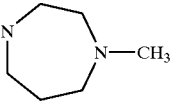 |
| A164 | 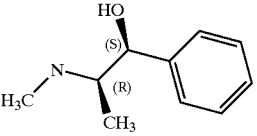 |
| A165 | 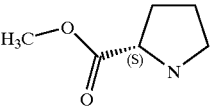 |
| A166 | 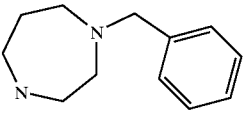 |
| A167 | 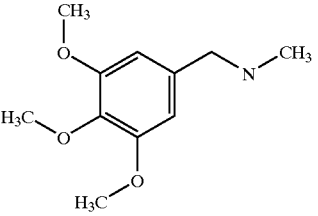 |
| A168 | 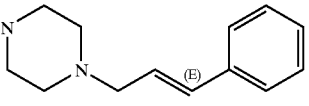 |
| A169 | 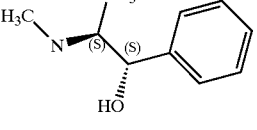 |
| A170 | 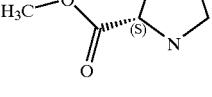 |
| A171 | 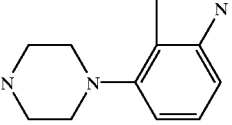 |

-continued

| No. | L₂ |
|---|---|
| A172 | (S)-N-methyl, (R)-phenyl, HO — H₃C-NH-CH(CH₃)-CH(OH)-C₆H₅ |
| A173 | piperazine-pyrimidin-2-yl |
| A174 | 1-methyl-4-(piperazin-1-yl)piperidine |
| A175 | (R)-1-(isopropylamino)-3-(naphthalen-1-yloxy)propan-2-ol |
| A176 | (S)-2-(pyrrolidin-1-ylmethyl)pyrrolidine |
| A177 | 1-(3-phenylpropyl)piperazine |
| A178 | (S)-1-(isopropylamino)-3-(naphthalen-1-yloxy)propan-2-ol |
| A179 | HO-CH₂CH₂-NH-(CH₂)₄-CH₃ |
| A180 | 1-(2-(piperidin-1-yl)ethyl)piperazine |
| A181 | (R)-2-(methoxymethyl)pyrrolidine |
| A182 | 2-methylpyrrolidine |
| A183 | 4-(3-(piperazin-1-yl)propyl)morpholine |
| A184 | (2R,6S)-2,6-dimethylpiperidine |

-continued

| No. | L₂ |
|---|---|
| A185 | piperidin-3-ol |
| A186 | 2-(piperazin-1-yl)-1H-benzimidazole |
| A187 | (S)-N-benzyl-1-phenylethanamine (N-benzyl) |
| A188 | H₃C-NH-CH₂CH₂-N(CH₃)₂ |
| A189 | 2-(piperazin-1-ylmethyl)-1H-benzimidazole |
| A190 | (1R,4S)-1,3,3-trimethyl-2-azabicyclo[2.2.1]heptane |
| A191 | H₃C-NH-(CH₂)₃-N(CH₃)₂ |
| A192 | N-ethyl-1-(furan-2-yl)-2-phenylethanamine |
| A193 | 1-(2-(thiophen-2-yl)ethyl)piperazine |
| A194 | (2S,6R)-2,6-dimethylmorpholine |
| A195 | CH₃-NH-CH₂-(furan-2-yl) |

-continued
| No. | L₂ |
|---|---|
| A196 | 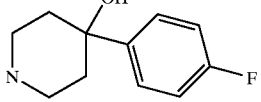 |
| A197 | 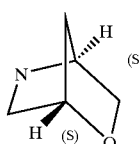 |
| A198 | 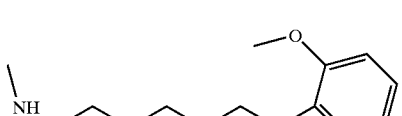 |
| A199 | 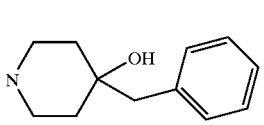 |
| A200 | 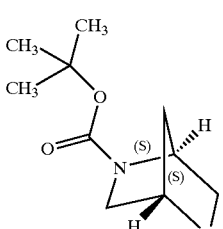 |
| A201 | 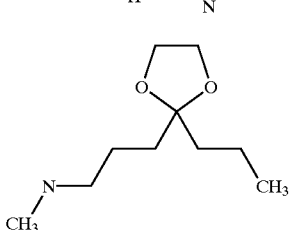 |
| A202 | 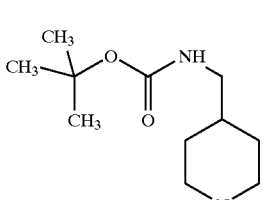 |
| A203 | 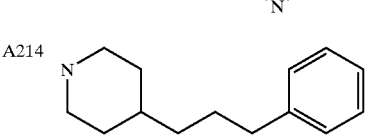 |
| A204 | 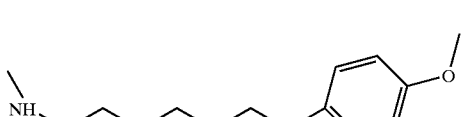 |
| A205 | 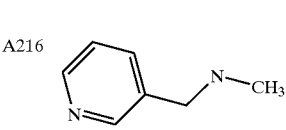 |
| A206 | |
-continued
| No. | L₂ |
|---|---|
| A207 | |
| A208 | |
| A209 | |
| A210 | |
| A211 | |
| A212 | |
| A213 | |
| A214 | |
| A215 | |
| A216 | |

-continued

| No. | L₂ |
|---|---|
| A217 | [1-(5-nitropyridin-2-ylmethyl)-1,4-diazepane] |
| A218 | [N-(pyridin-4-ylmethyl)-N-(3-hydroxypropyl)amine] |
| A219 | [(R)-3,4-dihydroxy-α-((methylamino)methyl)benzyl alcohol] |
| A220 | [N-methyl-1-(1,3-dioxolan-2-yl)methanamine] |
| A221 | [N,N,N'-trimethyl-1,3-propanediamine] |
| A222 | [4-hydroxy-α-((methylamino)methyl)benzyl alcohol] |
| A223 | [N-methyl-2-(pyridin-2-yl)ethylamine] |
| A224 | [N,N,N'-trimethylamine (ethyl)] |
| A225 | [2-chloro-N-methylbenzylamine] |
| A226 | [N,N,N'-trimethyl-1,2-ethanediamine] |
| A227 | [10,11-dihydro-5H-dibenz[b,f]azepine-5-propanamine, N-methyl-] |
| A228 | [3-(10,11-dihydro-5H-dibenzo[a,d]cyclohepten-5-ylidene)-N-methylpropan-1-amine] |
| A229 | [3,4-dimethoxy-N-methylphenethylamine] |
| A230 | [(R)-N-methyl-1-(naphthalen-1-yl)ethanamine] |
| A231 | [2,4-dichloro-N-methylbenzylamine] |
| A232 | [3-hydroxy-N-methyl-3-phenylpropan-1-amine] |
| A233 | [4-nitro-N-methylphenethylamine] |
| A234 | [1-(2,6-dimethoxybenzyl)-N-methylpiperidin-4-amine] |
| A235 | [N-methyl-1-(naphthalen-1-yl)methanamine] |

-continued

| No. | L₂ |
|---|---|
| A236 | 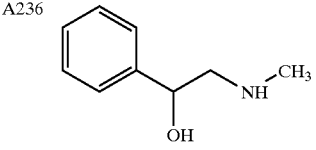 |
| A237 | 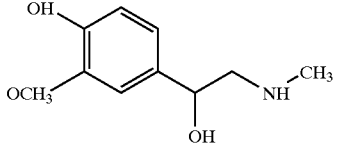 |
| A238 | 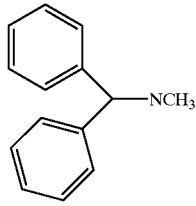 |
| A239 | OH⌒⌒N(CH₃)₂ |
| A240 | (CH₃)₂N—CH₂CH₃ |
| A241 | CH₃NH—CH₂CH₃ |

Preferably, L₂ can also be a group of formula A301-A439 as shown in the following table. L₂ is preferably linked to X through a non-aromatic nitrogen atom (e.g. a secondary amino nitrogen) of L₂.

| No. | |
|---|---|
| A301 | 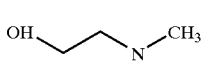 |
| A302 | 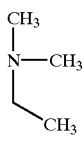 |
| A303 | 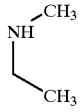 |
| A304 | —NH⌒⌒⌒ |
| A305 | 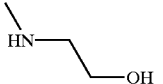 |
| A306 | 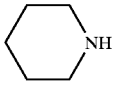 |
| A307 | 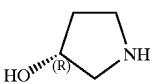 |
| A308 | HO-piperidine-NH (3-hydroxypiperidine) |
| A309 | HO-piperidine-NH (4-hydroxypiperidine) |
| A310 | (R)-2-(hydroxymethyl)pyrrolidine |
| A311 | (S)-2-(hydroxymethyl)pyrrolidine |
| A312 | HO⌒⌒NH⌒⌒OH |
| A313 | 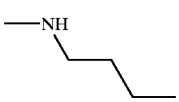 |
| A314 | cyclopropylmethyl-NH-propyl |
| A315 | 2-isopropylpyrrolidine |

| | | | | |
|---|---|---|---|---|
| A316 | 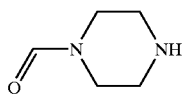 | | A328 | 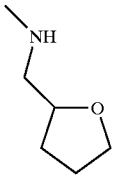 |
| A317 | 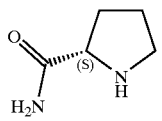 | | | |
| | | | A329 | 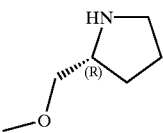 |
| A318 | 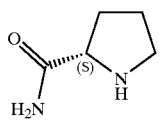 | | | |
| | | | A330 | 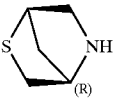 |
| A319 | 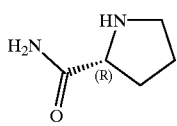 | | | |
| | | | A331 | 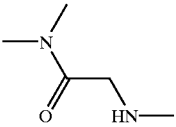 |
| A320 | 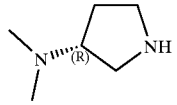 | | | |
| | | | A332 | 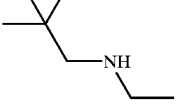 |
| A321 | 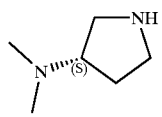 | | | |
| | | | A333 | 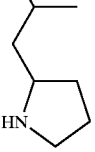 |
| A322 | 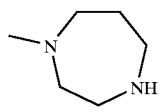 | | | |
| | | | A334 | 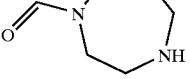 |
| A323 | 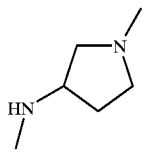 | | | |
| | | | A335 | 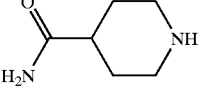 |
| A324 | 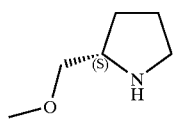 | | | |
| | | | A336 | 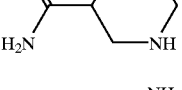 |
| A325 | 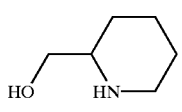 | | | |
| | | | A337 | 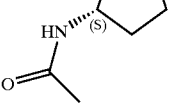 |
| A326 | 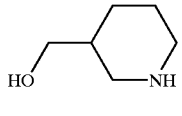 | | | |
| A327 | 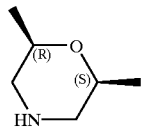 | | A338 | 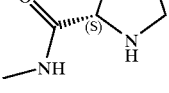 |

-continued
A339 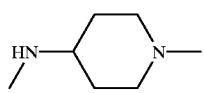
A340 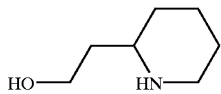
A341 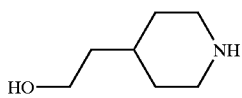
A342 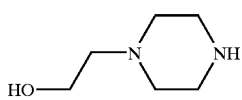
A343 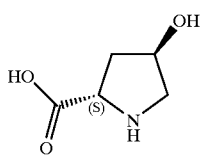
A344 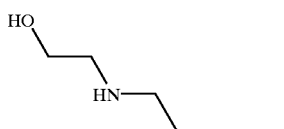
A345 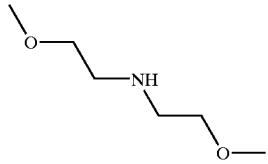
A346 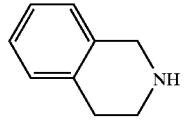
A347 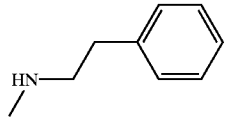
A348 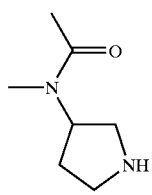
A349 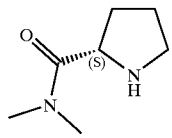
-continued
A350 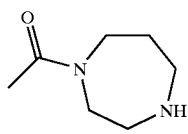
A351 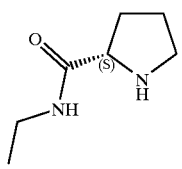
A352 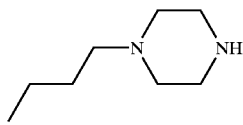
A353 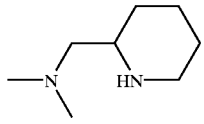
A354 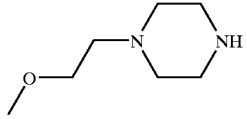
A355 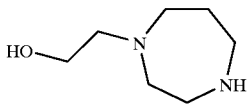
A356 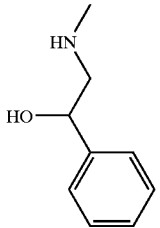
A357 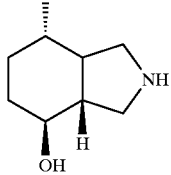
A358 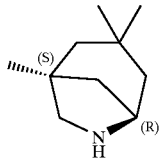

-continued
| | |
|---|---|
| A359 | 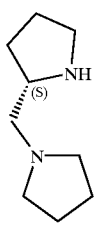 |
| A360 | 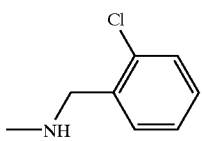 |
| A361 | 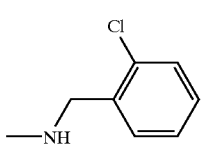 |
| A362 | 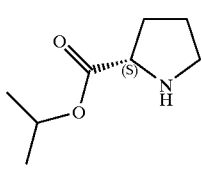 |
| A363 | 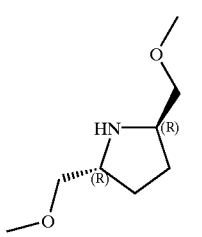 |
| A364 | 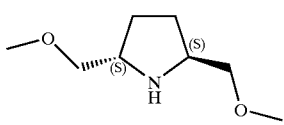 |
| A365 | 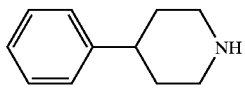 |
| A366 | 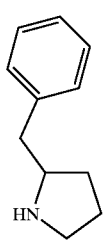 |
| A367 | 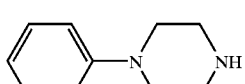 |
| A368 | 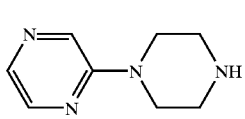 |
-continued
| | |
|---|---|
| A369 | 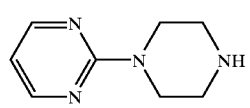 |
| A370 | 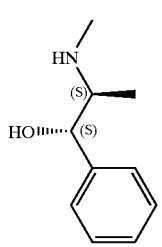 |
| A371 | 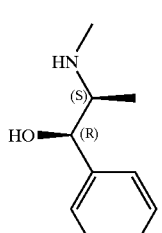 |
| A372 | 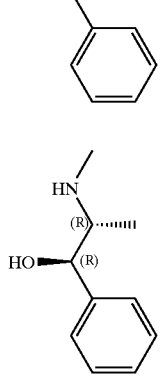 |
| A373 |  |
| A374 | 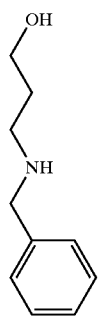 |

-continued
A375 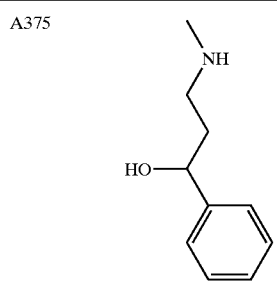
A376 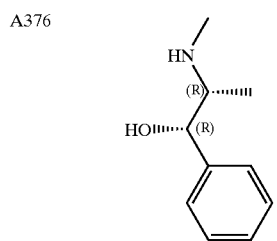
A377 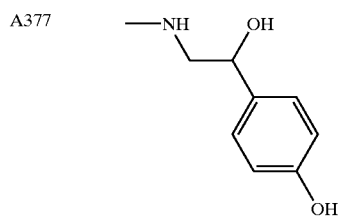
A378 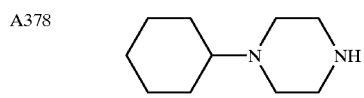
A379 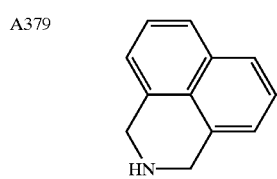
A380 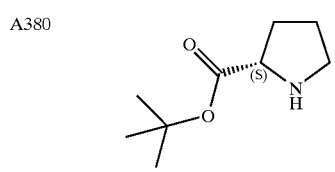
A381 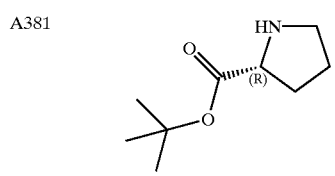
A382 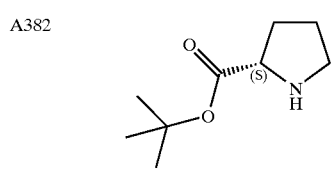
-continued
A383 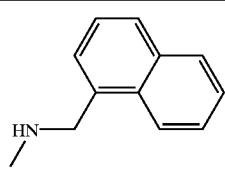
A384 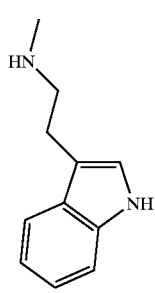
A385 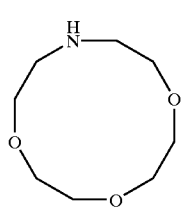
A386 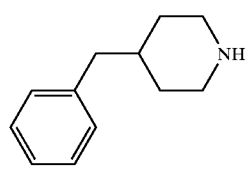
A387 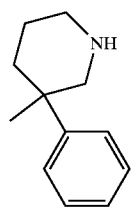
A388 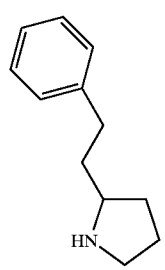
A389 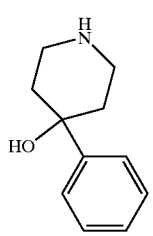

| | |
|---|---|
| A390 | 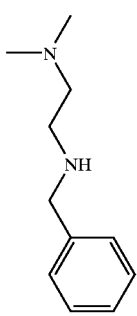 |
| A391 | 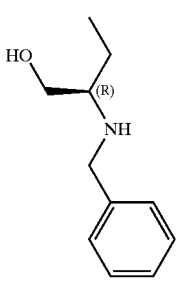 |
| A393 | 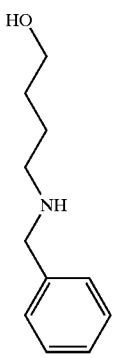 |
| A394 | 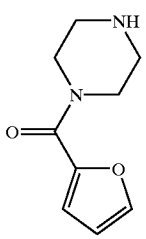 |
| A395 | 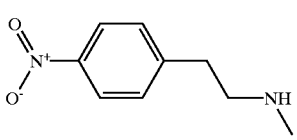 |
| A396 | 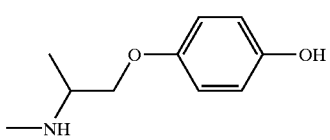 |
| A397 | 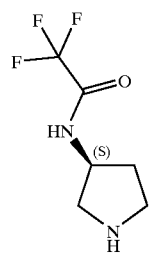 |
| A398 | 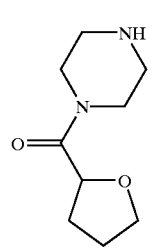 |
| A399 | 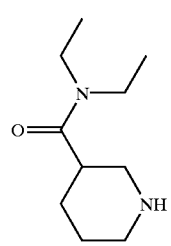 |
| A400 | 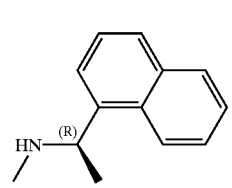 |
| A401 | 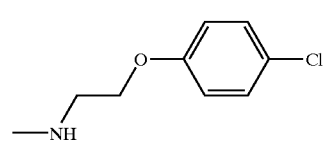 |
| A402 | 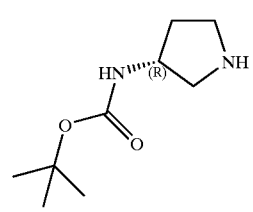 |
| A403 | 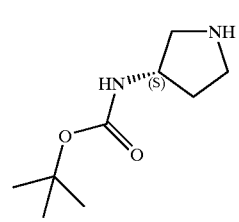 |

-continued
A404 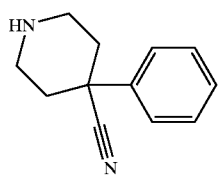
A405 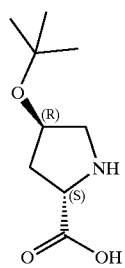
A406 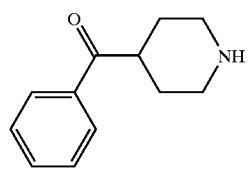
A407 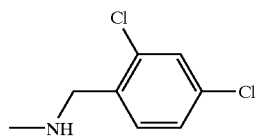
A408 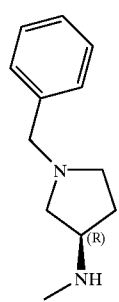
A409 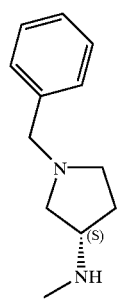
A410 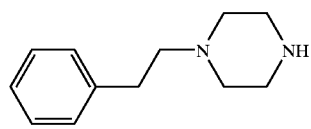
-continued
A411 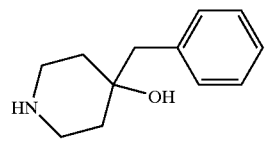
A412 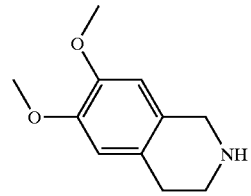
A413 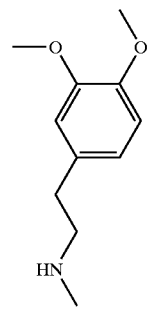
A414 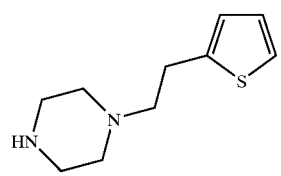
A415 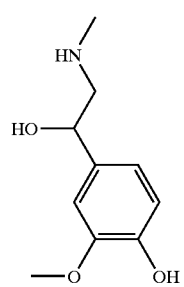
A416 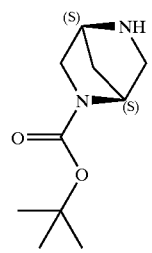
A417 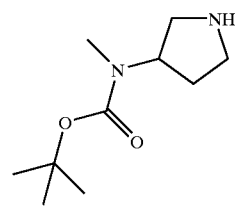

-continued
A418 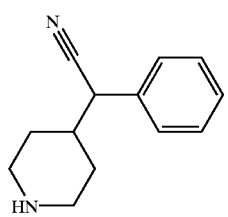
A419 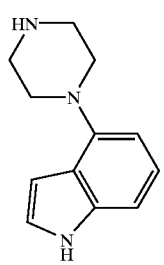
A420 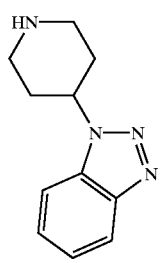
A421 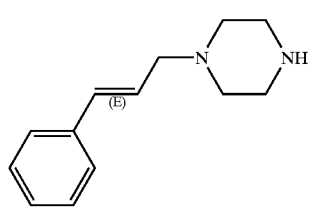
A422 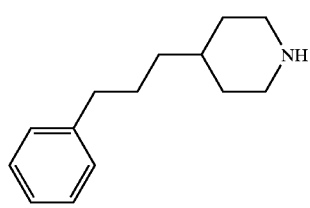
A423 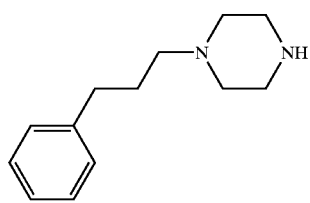
A424 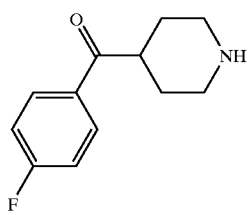
-continued
A425 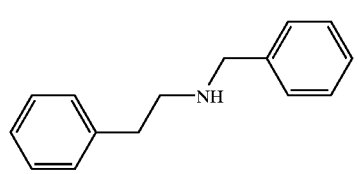
A426 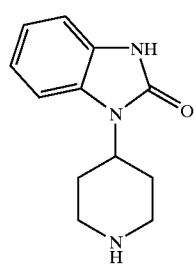
A427 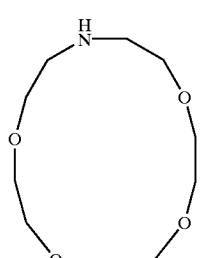
A428 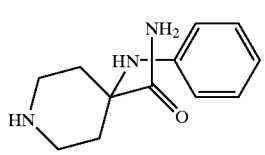
A429 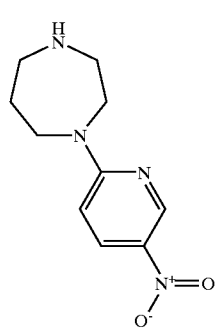
A430 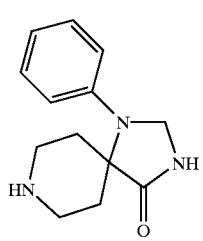

-continued
A431 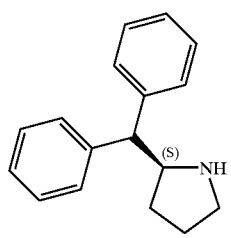
A432 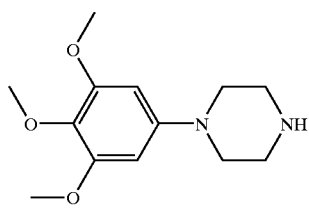
A433 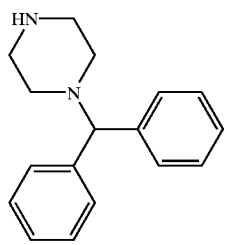
A434 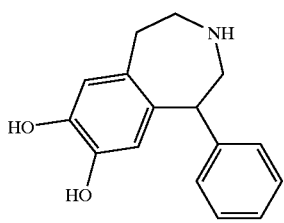
A435 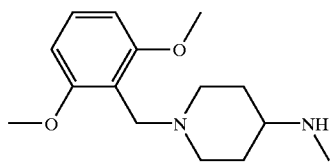
A436 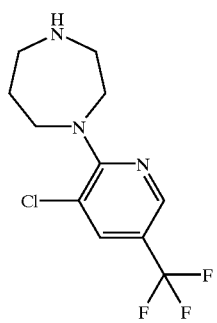
-continued
A437 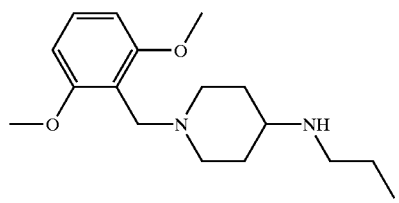
A438 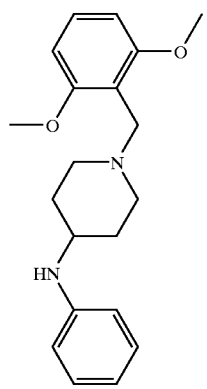
A439 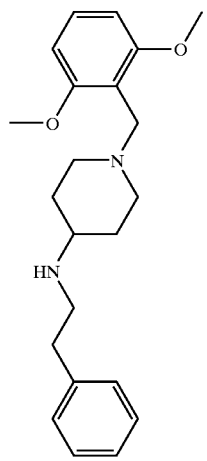
Preferably, $L_2$ can also be a group of formula A501-A523 as shown in the following table. $L_2$ is preferably linked to X through a non-aromatic nitrogen atom of $L_2$.
| No. | $L_2$ |
|---|---|
| A501 | 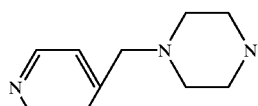 |
| A502 | 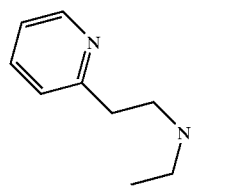 |

-continued
| No. | L₂ |
|---|---|
| A503 | 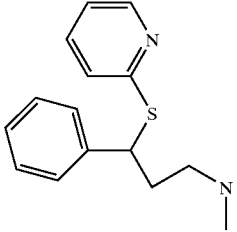 |
| A504 | 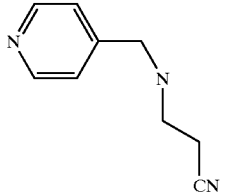 |
| A505 | 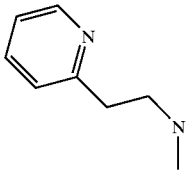 |
| A506 | 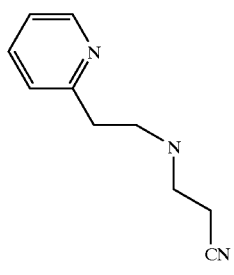 |
| A507 | 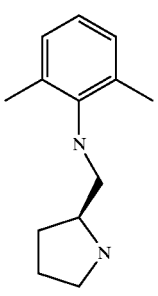 |
| A508 | 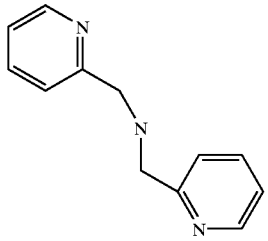 |
| A509 | 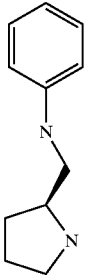 |
| A510 | 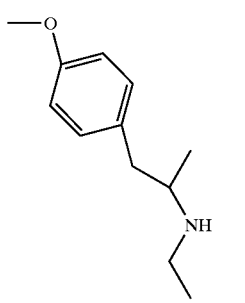 |
-continued
| No. | L₂ |
|---|---|
| A511 |  |
| A512 | 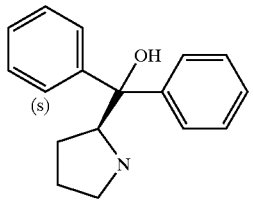 |
| A513 | 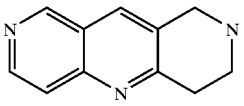 |
| A514 | 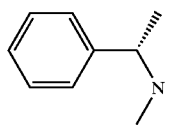 |
| A515 | 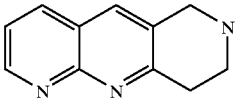 |
| A516 | 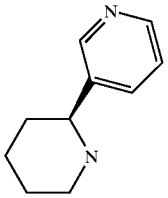 |

-continued
| No. | L$_2$ |
|---|---|
| A517 | 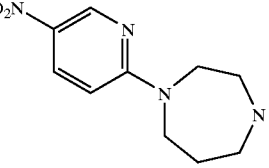 |
| A518 | 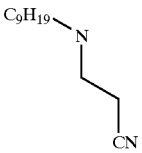 |
| A519 | 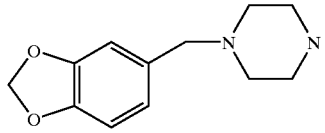 |
| A520 | 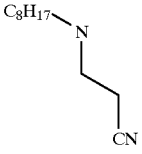 |
| A521 | 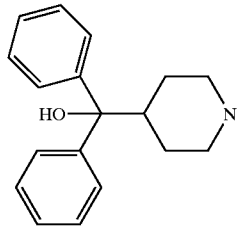 |
| A522 |  |
| A523 |  |
| A524 | 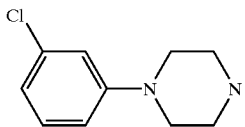 |
-continued
| No. | L$_2$ |
|---|---|
| A525 | 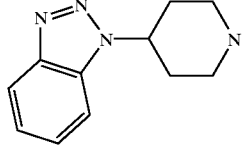 |
| A526 | 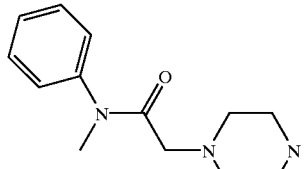 |
| A527 | 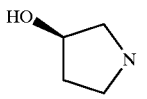 |
| A528 | 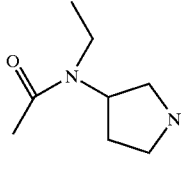 |
| A529 | |
| A530 | |
| A531 | |
| A532 | |
| A533 | |
| A534 | |

-continued

| No. | L₂ |
|---|---|
| A535 | 1-phenyl-2,3,4,5-tetrahydro-1H-3-benzazepine-7,8-diol |
| A536 | (1R,2S)-2-(methylamino)-1-phenylpropan-1-ol |
| A537 | (1S,2S)-2-(methylamino)-1-phenylpropan-1-ol |
| A538 | 1-benzyl-N-methylpyrrolidin-3-amine |
| A539 | 1-benzyl-N-methylpyrrolidin-3-amine (diastereomer) |
| A540 | 4-phenyl-4-cyanopiperidine |
| A541 | benzyl 2-(methylamino)acetate |

-continued

| No. | L₂ |
|---|---|
| A542 | C₁₂H₂₅−NH−CH₂CH₂−C(O)−CH₃ |
| A543 | 2-(4-nitrophenyl)-N-methylethanamine |
| A544 | N-(2,6-dimethylphenyl)-1-(pyrrolidin-2-yl)methanamine |
| A545 | tert-butyl methyl(pyrrolidin-3-yl)carbamate |
| A546 | benzyl 2-(methylamino)acetate |
| A547 | piperidine-4-carboxamide |
| A548 | 4,5,6,7-tetrahydro-3H-imidazo[4,5-c]pyridine-6-carboxylic acid |
| A549 | N,N-dimethyl-1-(piperidin-2-yl)methanamine |

-continued
| No. | L₂ |
|---|---|
| A550 | 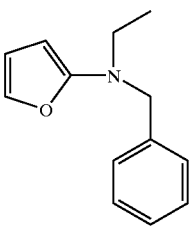 |
| A551 | 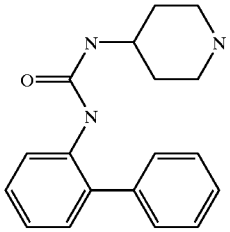 |
| A552 | 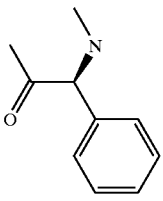 |
| A553 | 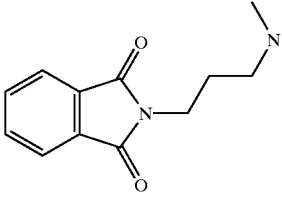 |
| A554 | 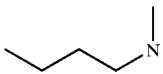 |
| A555 | 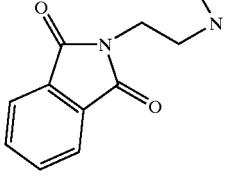 |
| A556 | 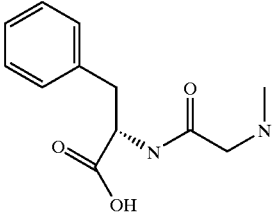 |
-continued
| No. | L₂ |
|---|---|
| A557 | 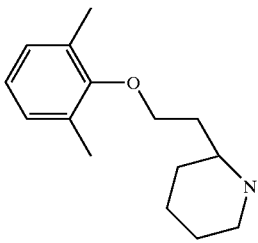 |
| A558 | 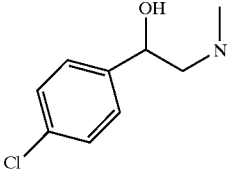 |
| A559 | 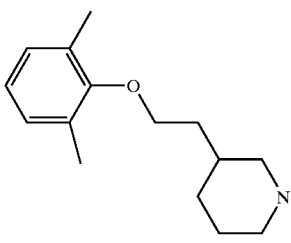 |
| A560 | 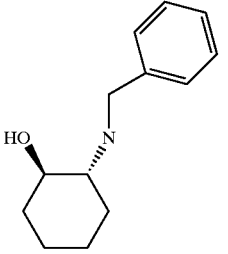 |
| A561 | 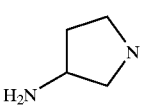 |
| A562 | 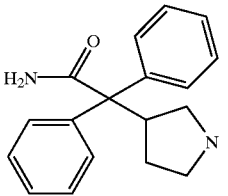 |
| A563 | 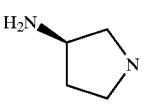 |
| A564 | 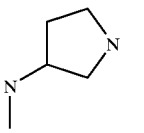 |

-continued
| No. | L₂ |
|---|---|
| A565 | 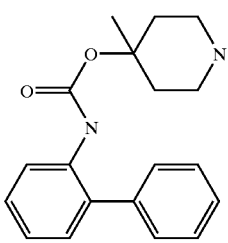 |
| A566 | 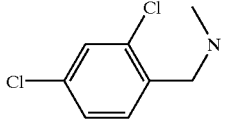 |
| A567 | 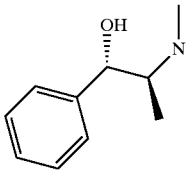 |
| A568 | 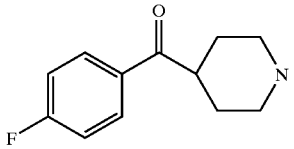 |
| A569 | 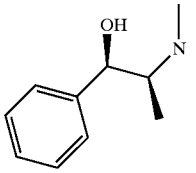 |
| A570 | 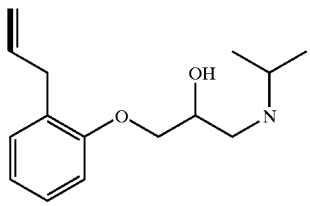 |
| A571 | 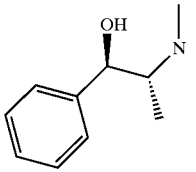 |
| A572 | 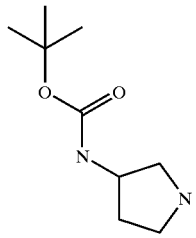 |
-continued
| No. | L₂ |
|---|---|
| A573 | 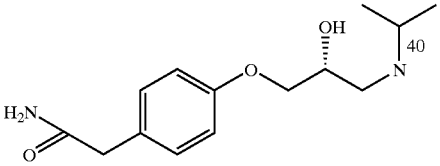 |
| A574 | 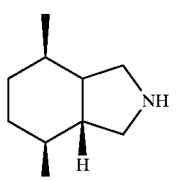 |
| A575 | 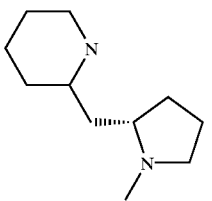 |
| A576 | 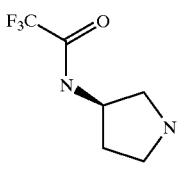 |
| A577 | 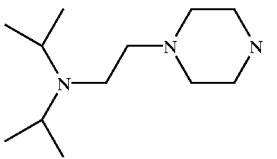 |
| A578 | 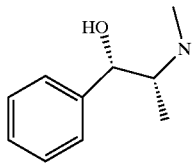 |
| A579 | 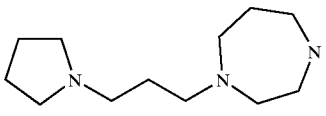 |
| A580 | 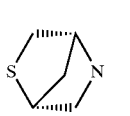 |
| A581 | 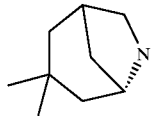 |

-continued

| No. | L₂ |
|---|---|
| A582 |  |
| A583 | 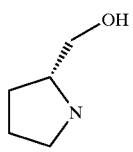 |
| A584 | 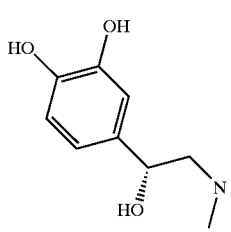 |
| A585 | 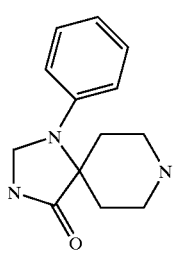 |
| A586 | 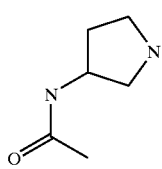 |
| A587 |  |
| A588 | 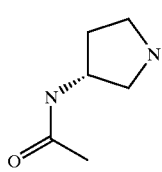 |
| A589 | 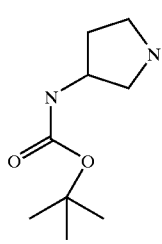 |

-continued

| No. | L₂ |
|---|---|
| A590 | 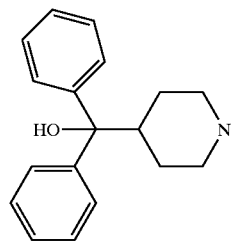 |

A more preferred value for $L_2$ is A234, A363, A364, A153, A28, A324, A329, A562, A87, or A239.

A preferred value for X is alkylene optionally substituted with one, two, or three hydroxy groups, alkylene wherein one, two or three carbon atoms have been replaced by an oxygen atom, -alkylene-phenylene-alkylene- wherein the phenylene ring is optionally substituted with one or two chloro or fluoro groups.

Another preferred value for X is an alkylene group having from 3 to 20 carbon atoms; wherein one or more carbon atoms (e.g. 1, 2, 3, or 4) in the alkylene group is optionally replaced with —O—; and wherein the chain is optionally substituted on carbon with one or more hydroxyl (e.g. 1, 2, 3, or 4).

Another preferred value for X is an alkylene group having from 6 to 15 carbons atoms; wherein one or more carbon atoms (e.g. 1, 2, 3, 4) in the alkylene group is optionally replaced with —O—; and wherein the chain is optionally substituted on carbon with one or more hydroxyl (e.g. 1, 2, 3, or 4).

Another preferred value for X is is nonane-1,9-diyl, octane-1,8-diyl, propane-1,3-diyl, 2-hydroxypropane-1,3-diyl, or 5-oxa-nonane-1,9-diyl.

Another preferred value for X is a group of the following formula:

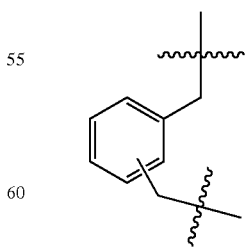

wherein the phenyl ring is optionally substituted with 1, 2, or 3 fluoro groups.

Another preferred value for X is a group of one of the following formulae:

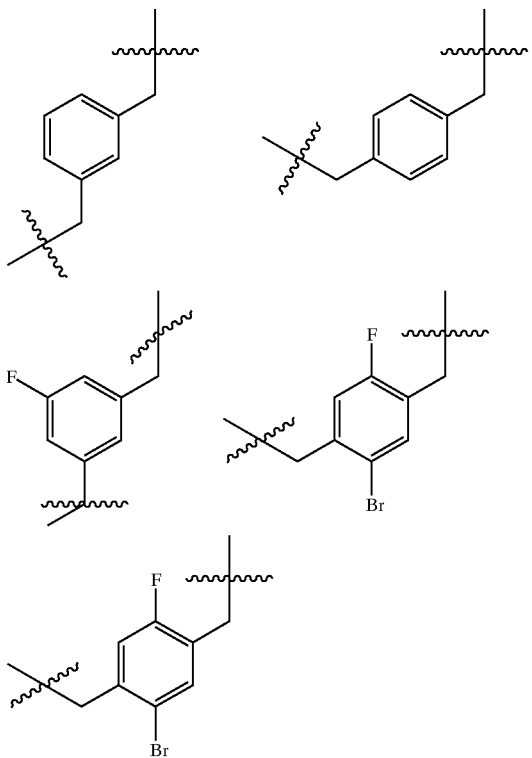

A preferred group of compounds of formula (I) are compounds wherein $R^2$ is selected from formula (i) and (iii); and wherein K" is a bond or methylene.

A preferred group of compounds of formula (I) are compounds wherein $R^2$ is formula (i); $R^3$ is hydrogen, methyl, ethyl, propyl, isopropyl, fluoro, or trifluoromethyl; and K" is a bond or methylene.

A preferred group of compounds of formula (I) are compounds wherein $R^2$ is formula (iii); $R^6$, $R^7$, and $R^8$ are each hydrogen, methyl, ethyl, propyl, isopropyl, fluoro, or trifluoromethyl; and K" is a bond or methylene.

A preferred group of compounds are compounds of formula (I) wherein $R^{46}$ is alkyl, substituted alkyl, cycloalkyl, substituted cycloalkyl, or heterocycle; $R^{47}$ is alkyl, substituted alkyl, aryl, acyl, heterocycle, or —COOR$^{50}$ where $R^{50}$ is alkyl; or $R^{46}$ and $R^{47}$ together with the nitrogen atom to which they are attached form heterocycle.

A preferred group of compounds are compounds of formula (I) wherein $L_2$ is a group of formula (d) wherein $R^{46}$ and $R^{47}$ together with the nitrogen atom to which they are attached form heterocycle which is substituted with 1 to 5 substituents independently selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl —SO$_2$-heteroaryl, alkyl, substituted alkyl, alkenyl, substituted alkenyl, alkynyl, and substituted alkynyl.

A more preferred group of compounds are compounds of formula (I) wherein $L_2$ is a group of formula (d) wherein $R^{46}$ and $R^{47}$ together with the nitrogen atom to which they are attached form heterocycle which is substituted with 1 to 3 substituents independently selected from the group consisting of alkoxy, substituted alkoxy, acyl, acylamino, acyloxy, amino, substituted amino, aminoacyl, aminoacyloxy, oxyaminoacyl, cyano, halogen, hydroxyl, keto, thioketo, carboxyl, carboxylalkyl, hydroxyamino, alkoxyamino, alkyl, substituted alkyl, alkenyl, substituted alkenyl, alkynyl, and substituted alkynyl.

A preferred group of compounds are compounds of formula (I) wherein $L_2$ is a group of formula (d) wherein $R^{46}$ and $R^{47}$ together with the nitrogen atom to which they are attached form heterocycle which is substituted with 1 to 5 substituents independently selected from the group consisting of substituted alkyl, alkenyl, substituted alkenyl, alkynyl, and substituted alkynyl.

A preferred group of compounds are compounds of formula (I) wherein $L_2$ is a group of formula (d) wherein at least one of $R^{46}$ and $R^{47}$ individually, or $R^{46}$ and $R^{47}$ taken together, is a group that comprises a basic nitrogen atom (e.g. a nitrogen atom with a pKa of preferably at least about 5, more preferably al least about 6, or most preferably at least about 7).

A preferred group of compounds are compounds of formula (I) wherein $L_2$ is a group of formula (d) wherein $R^{46}$ is a heterocycle, optionally substituted with 1 to 5 substituents independently selected from the group consisting of alkyl, substituted alkyl, alkenyl, substituted alkenyl, alkynyl, and substituted alkynyl; and $R^{47}$ is alkyl, substituted alkyl, acyl, or —COOR$^{50}$.

A preferred group of compounds are compounds of formula (1) wherein $L_2$ is a group of formula (d) wherein $R^{46}$ is alkyl that is substituted by a group that comprises a basic nitrogen atom (e.g. a nitrogen atom with a pKa of preferably at least about 5, more preferably al least about 6, or most preferably at least about 7).

A preferred group of compounds are compounds of formula (I) wherein $L_2$ is a group of formula (d) wherein $R^{46}$ is alkyl that is optionally substituted with from 1 to 5 substituents independently selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, cyano, halogen, hydroxyl, keto, thioketo, carboxylalkyl, thioaryloxy, thioheteroaryloxy, thioheterocyclooxy, thiol, thioalkoxy, substituted thioalkoxy, heterocyclic, heterocyclooxy, hydroxyamino, alkoxyamino, NR$^a$R$^b$, wherein R$^a$ and R$^b$ may be the same or different and and are chosen from hydrogen, alkyl, substituted alkyl, cycloalkyl, alkenyl, cycloalkenyl, alkynyl, and heterocyclic.

A preferred group of compounds are compounds of formula (I) wherein $L_2$ is a group of formula (d) wherein $R^{46}$ is a heterocycle which is optionally substituted with 1 to 5 substituents independently selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$- substituted alkyl, —SO$_2$-aryl —SO$_2$-heteroaryl, alkyl, substituted alkyl, alkenyl, substituted alkenyl, alkynyl, and substituted alkynyl.

A preferred group of compounds are compounds of formula (I) wherein L$_2$ is a group of formula (d) wherein R$^{46}$ is 3-piperidinyl, 4-piperidinyl, or 3-pyrrolidinyl, which R$^{46}$ is optionally substituted with 1 to 3 substituents independently selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, cyano, halogen, hydroxyl, keto, thioketo, carboxylalkyl, thioaryloxy, thioheteroaryloxy, thioheterocyclooxy, thiol, thioalkoxy, substituted thioalkoxy, heterocyclic, heterocyclooxy, hydroxyamino, alkoxyamino, alkyl, substituted alkyl, alkenyl, substituted alkenyl, alkynyl, and substituted alkynyl.

A preferred group of compounds are compounds of formula (I) wherein R$^{46}$ and R$^{47}$ together with the nitrogen atom to which they are attached form a piperidine or pyrrolidine ring which ring is optionally substituted with 1 to 3 substituents independently selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, cyano, halogen, hydroxyl, keto, thioketo, carboxylalkyl, thioaryloxy, thioheteroaryloxy, thioheterocyclooxy, thiol, thioalkoxy, substituted thioalkoxy, heterocyclic, heterocyclooxy, hydroxyamino, alkoxyamino, alkyl, substituted alkyl, alkenyl, substituted alkenyl, alkynyl, and substituted alkynyl.

A preferred group of compounds are compounds of formula (I) wherein R$^{46}$ and R$^{47}$ together with the nitrogen atom to which they are attached form a heterocycle that is an aza-crown ether (e.g. 1-aza-12-crown-4, 1-aza-15-crown-5, or 1-aza-18-crown-6).

A preferred group of compounds of formula (I) are compounds wherein: A is an aryl or a heteroaryl ring; B" is —NRa— wherein Ra is hydrogen, alkyl, or substituted alkyl; R$^1$ is hydrogen or alkyl; R$^2$ is selected from a group consisting of formula (i), (ii), (iii), or "Het":
wherein: —is an optional double bond; n, is an integer of from 1 to 4; n$_2$ is an integer of from 1 to 3; V is —CH—, —O—, —S(O)n$_3$— (where n$_3$ is an integer of from 0 to 2), or —NR$^4$— (wherein R$^4$ is hydrogen, alkyl, substituted alkyl, aryl, or heteroaryl); "Het" is a heteroaryl ring which optionally attaches the ligand to a linker; R$^3$ is hydrogen, alkyl, amino, substituted amino, —OR$^a$ (where R$^a$ is hydrogen, alkyl, or acyl), or a covalent bond attaching the ligand to a linker; R$^5$ is hydrogen, alkyl, amino, substituted amino, —OR$^b$ (where R$^b$ is hydrogen or alkyl), aryl, aralkyl, heteroaralkyl, or a covalent bond attaching the ligand to a linker; R$^6$, R$^7$, and R$^8$ are, independently of each other, hydrogen, halo, hydroxy, alkoxy, haloalkoxy, carboxy, alkoxycarbonyl, alkyl optionally substituted with one, two or three substituents selected from halo, hydroxy, carboxy, alkoxycarbonyl, alkylthio, alkylsulfonyl, amino, substituted amino, or a covalent bond attaching the ligand to a linker; K is a bond or an alkylene group; K" is a bond, —C(O)—, —S(O)$_{n4}$— (where n$_4$ is an integer of from 0 to 2), or an alkylene group optionally substituted with a hydroxyl group; and B is a heterocycloamino group which optionally attaches the ligand to a linker; provided that at least one of the R$^5$, R$^6$, R$^7$, R$^8$, "Het", or the heterocycloamino group attaches the ligand to a linker.

A preferred compound of formula (I) is a compound of Formula (Ia):

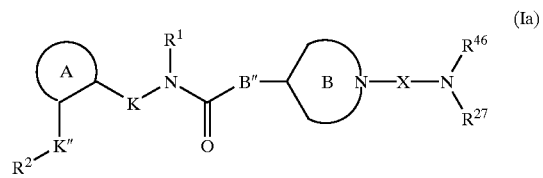

(Ia)

wherein A, R$^1$, R$^2$, K, K", B, X, R$^{46}$ and R$^{47}$ are as defined herein.

For a compound of Formula (Ia) a preferred group of compounds is that wherein A is phenyl or pyridine; and K and K" are bond.

For a compound of Formula (Ia) another preferred group of compounds is that wherein A is phenyl or pyridine; R$^2$ is phenyl; and K and K" are bond.

For a compound of Formula (Ia) another preferred group of compounds is that wherein B has any of the preferred values identified herein.

The invention also provides a compound of formula (IV):

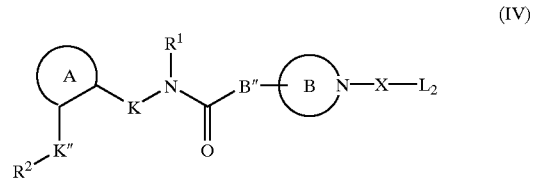

(IV)

wherein L$_2$ is an organic group comprising at least one (e.g. 1, 2, 3, or 4) primary, secondary, or tertiary amines. Typically, the amine of L$_2$ should be basic, having a pH of at least about 5, and preferably at least about 6, more preferably at least about 7. The nature of the group L$_2$ is not critical provided the compound has suitable properties (e.g. solubility, stability, and toxicity) for its intended use (e.g. as a drug or as a pharmacological tool). Typically the group L$_2$ will have a molecular weight below 500 and preferably below about 300. Additionally, the group L$_2$ preferably comprises 5 or fewer hydrogen bond donors (e.g. OH, —NHR—, and —C(═O)NHR—) and ten or fewer hydrogen bond acceptors (e.g. —O—, —NRR—, and —S—). Preferably, the nitrogen of B shown in formula (IV) is separated from an amine of the group L$_2$ by about 15 angstroms to about 75 angstroms (based on conventionally acceptable bond lengths and angles). More preferably, the nitrogen of B is separated from an amine of the group L$_2$ by about 25 angstroms to about 50 angstroms. Preferred compounds of formula (IV) also have a log D between about −3 and about 5. Using the above parameters, one skilled in the art can readily determine compounds of formula (IV) possessing the desired properties for an intended use.

General Synthetic Schemes

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989).

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Furthermore, it will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, New York, 1991, and references cited therein.

These schemes are merely illustrative of some methods by which the compounds of this invention can be synthesized, and various modifications to these schemes can be made and will be suggested to one skilled in the art having referred to this disclosure.

Preparation of a Compound of Formula (I)

In general, compounds of Formula (I) can be prepared as illustrated and described in Schemes A.

Scheme A

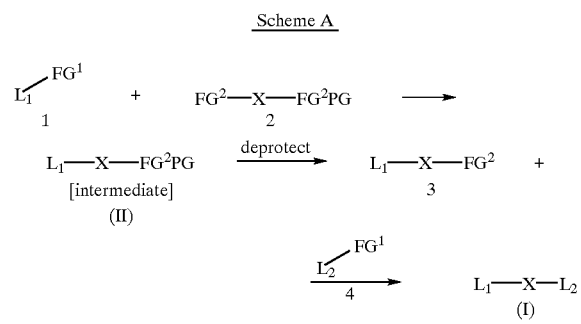

A compound of Formula (I) is prepared by covalently attaching one equivalent of a compound of formula 1 with a compound of formula 2 where X is a linker as defined herein, $FG^1$ is a functional group, $FG^2$ is a functional group that is complimentary to $FG^1$, PG is a protecting group, and $FG^2PG$ is a protected functional group, to give an intermediate of formula (II). Deprotection of the functional group on the linker, followed by reaction of resulting compound 3 with one equivalent of compound 4, then provides a compound of Formula (I). The reaction conditions used to link compounds 1 and 4 to compound 2 and 3 depend on the nature of the functional groups on compounds 1, 2, 3 and 4 which in turn depend on the type of linkage desired. Examples of the functional groups and the reaction conditions that can be used to generate a specific linkage is described below.

TABLE I

Representative Complementary Binding Chemistries

| First Reactive Group | Second Reactive Group | Linkage |
|---|---|---|
| carboxyl | amine | amide |
| sulfonyl | halide amine | sulfonamide |
| hydroxyl | alkyl/aryl halide | ether |
| hydroxyl | isocyanate | urethane |
| amine | epoxide | β-hydroxyamine |
| amine | alkyl/aryl halide | alkylamine |
| hydroxyl | carboxyl | ester |

Reaction between a carboxylic acid of either the linker or the ligand and a primary or secondary amine of the ligand or the linker in the presence of suitable, well-known activating agents such as dicyclohexylcarbodiimide, results in formation of an amide bond covalently linking the ligand to the linker; reaction between an amine group of either the linker or the ligand and a sulfonyl halide of the ligand or the linker, in the presence of a base such as triethylamine, pyridine, and the like results in formation of a sulfonamide bond covalently linking the ligand to the linker; and reaction between an alcohol or phenol group of either the linker or the ligand and an alkyl or aryl halide of the ligand or the linker in the presence of a base such as triethylamine, pyridine, and the like, results in formation of an ether bond covalently linking the ligand to the linker.

Suitable dihydroxyl and dihalo starting materials useful for incorporating a group X into a compound of the invention are shown in the following table. Preferably, an alcohol is reacted with a ligand bearing a leaving group to provide an ether bond, while a dihalo compound is preferably reacted with an amine of the ligand to form a subatituted amine.

| No. | X |
|---|---|
| X1 |  |

-continued
| No. | X |
|---|---|
| X2 | 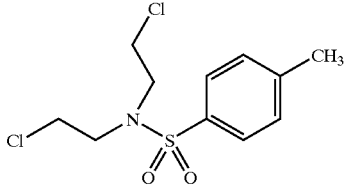 |
| X3 | 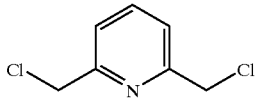 |
| X4 | 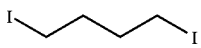 |
| X5 | 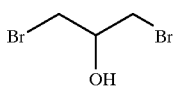 |
| X6 | 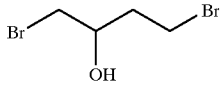 |
| X7 | 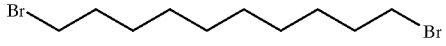 |
| X8 | 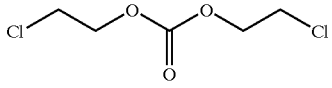 |
| X9 | 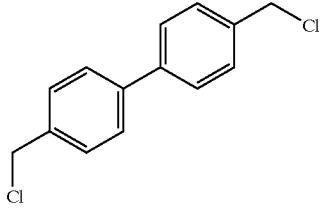 |
| X10 | 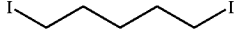 |
| X11 | 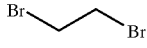 |
| X12 | 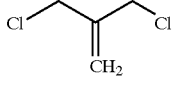 |
| X13 | 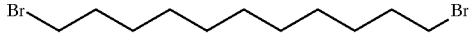 |
| X14 | 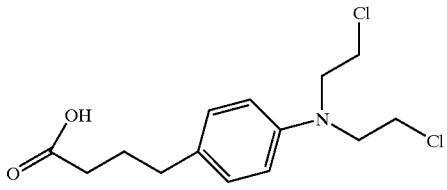 |
| X15 | 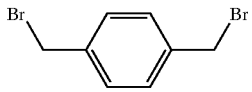 |

-continued

| No. | X |
|---|---|
| X16 | 10,11-dibromo-5H-dibenzo[a,d]cycloheptan-5-one |
| X17 | trans-1,2-dibromocyclohexane |
| X18 | I–CH$_2$CH$_2$CH$_2$–I (1,3-diiodopropane) |
| X19 | Br–(CH$_2$)$_{12}$–Br (1,12-dibromododecane) |
| X20 | diethyl 2,3-dibromoadipate (H$_3$C–O–C(O)–CHBr–CH$_2$CH$_2$–CHBr–C(O)–O–CH$_3$ with ethyl esters) |
| X21 | (1R,2R)-1,2-dibromo-1,2-diphenylethane |
| X22 | Cl–CH$_2$CH$_2$–N(CH$_3$)–CH$_2$CH$_2$–Cl · HCl (mechlorethamine hydrochloride) |
| X23 | 2,2-bis(bromomethyl)-1,3-propanediol (HO–CH$_2$–C(CH$_2$Br)$_2$–CH$_2$–OH) |
| X24 | CF$_3$–CHBr–CH$_2$Br (2,3-dibromo-1,1,1-trifluoropropane) |
| X25 | Br–(CH$_2$)$_7$–Br (1,7-dibromoheptane) |
| X26 | I–(CH$_2$)$_8$–I (1,8-diiodooctane) |
| X27 | tert-butyl 2,4-dibromobutanoate ((CH$_3$)$_3$C–O–C(O)–CHBr–CH$_2$–CH$_2$Br) |

-continued

| No. | X |
|---|---|
| X28 | 3,4-dibromo-tetrahydrothiophene 1,1-dioxide |
| X29 | 1,2,3-tribromopropane |
| X30 | cis-3,4-dichlorocyclobut-1-ene |
| X31 | Br-(CH₂)₆-Br (1,6-dibromohexane) |
| X32 | Br-CH₂CH₂-O-CH₂CH₂-Br |
| X33 | 2,2-dimethoxy-1,3-dibromopropane |
| X34 | 2,3-dibromopropanamide |
| X35 | 1,3-bis(chloromethyl)benzene |
| X36 | 1,4-dibromo-2-butene |
| X37 | Br-(CH₂)₁₀-Br |
| X38 | 1,5-dibromo-3-methylpentane |
| X39 | I-CH₂CH₂-O-CH₂CH₂-O-CH₂CH₂-I |
| X40 | N,N'-bis(2-chloroethyl)oxalamide |

-continued
| No. | X |
|---|---|
| X41 | 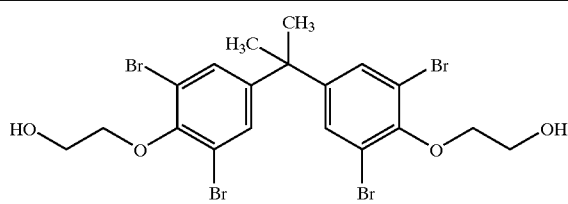 |
| X42 | 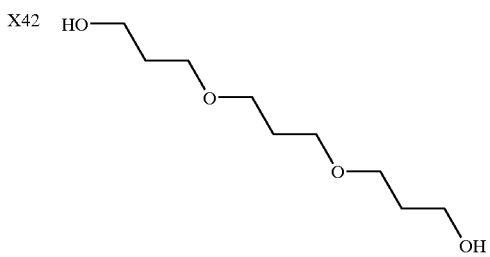 |
| X43 | 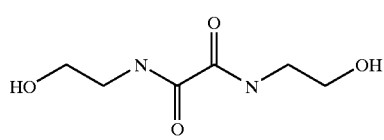 |
| X44 | 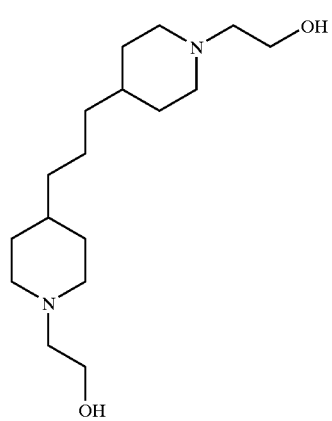 |
| X45 | 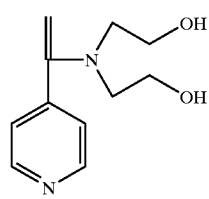 |
| X46 | 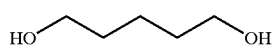 |
| X47 | 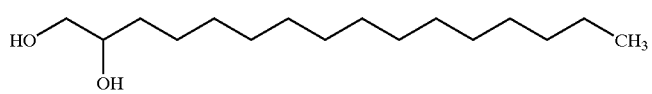 |
| X48 | 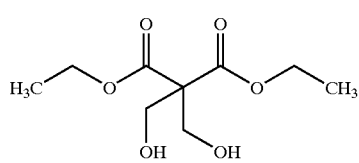 |

-continued
| No. | X |
|---|---|
| X49 | 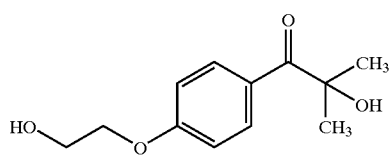 |
| X50 | 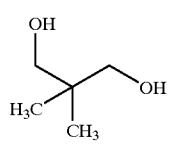 |
| X51 | 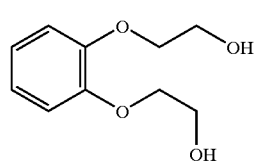 |
| X52 | 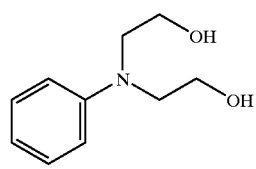 |
| X53 | 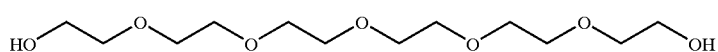 |
| X54 | 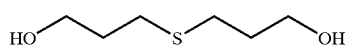 |
| X55 | HOCH$_2$(CF$_2$)$_8$CH$_2$OH |
| X56 | 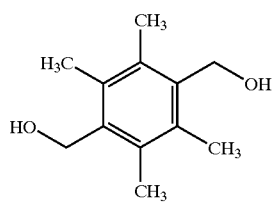 |
| X57 | 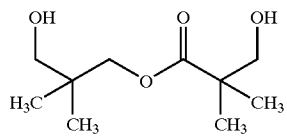 |
| X58 | 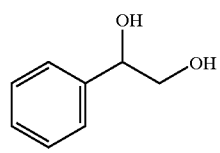 |
| X59 | 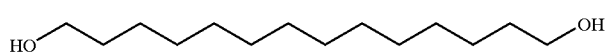 |
| X60 | 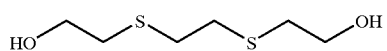 |

-continued

| No. | X |
|---|---|
| X61 | HOCH₂-(tricyclodecane)-CH₂OH |
| X62 | HOCH₂CH₂-S(=O)₂-CH₂CH₂OH |
| X63 | HOCH₂CH₂-S(=O)₂-CH₂CH₂OH |
| X64 | HO-CH₂CH₂CH₂-OH |
| X65 | HO-CH₂CH₂-O-CH₂CH₂-O-CH₂CH₂-O-CH₂CH₂-OH |
| X66 | HOCH₂CH₂-O-(1,4-C₆H₄)-O-CH₂CH₂OH |
| X67 | HO-(CH₂)₉-OH |
| X68 | HOCH₂-(1,3-C₆H₄)-CH₂OH |
| X69 | HOCH₂(CH₂)₄CH₂OH |
| X70 | HOCH₂-(2,6-pyridyl)-CH₂OH |
| X71 | HOCH₂CH₂-O-(C₆H₄)-C(fluorene)-(C₆H₄)-CH₂CH₂CH₂OH |
| X72 | HO-(CH₂)₇-OH |
| X73 | HO-(CH₂)₈-OH |
| X74 | H₃C-CH(OH)-(CH₂)₃-CH₂-OH |
| X75 | norbornene-2,3-bis(methanol) |

-continued
| No. | X |
|---|---|
| X76 | 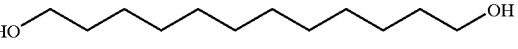 |
| X77 | 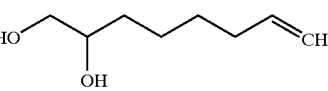 |
| X78 | 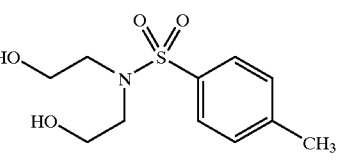 |
| X79 | 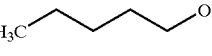 |
| X80 | 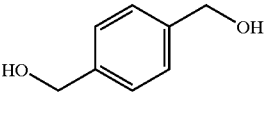 |
| X81 | 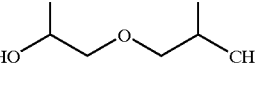 |
| X82 | 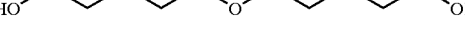 |
| X83 | 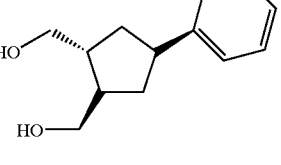 |
| X84 |  |
| X85 | 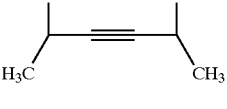 |
| X86 | 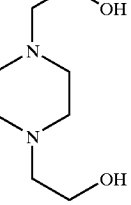 |
| X87 |  |

| No. | X |
|---|---|
| X88 | 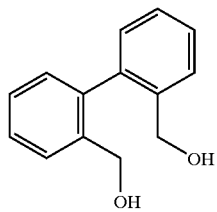 |
| X89 | 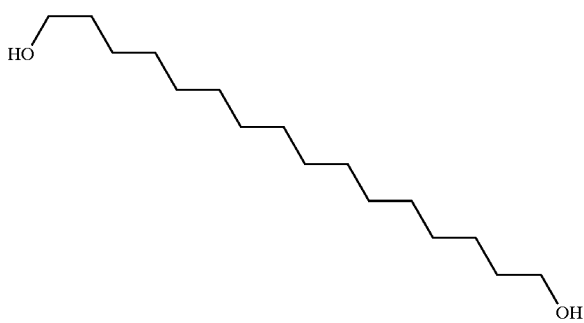 |
| X90 | 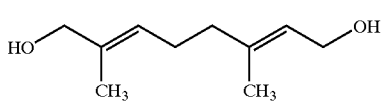 |
| X91 | 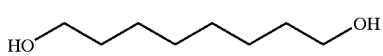 |
| X92 | 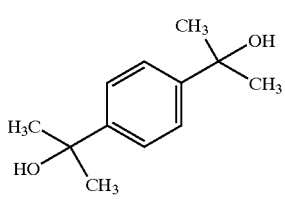 |
| X93 | 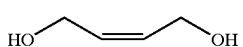 |
| X94 | 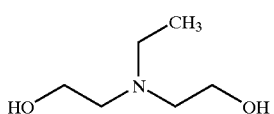 |
| X95 |  |
| X96 | 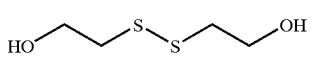 |
| X97 | 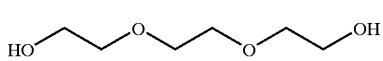 |
| X98 | 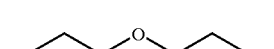 |
| X99 | 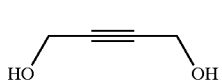 |
| X100 | $HOCH_2(CF_2)_3CH_2OH$ |

Typically, a compound selected for use as a ligand will have at least one functional group, such as an amino, hydroxyl, thiol or carboxyl group and the like, which allows the compound to be readily coupled to the linker. Compounds having such functionality are either known in the art or can be prepared by routine modification of known compounds using conventional reagents and procedures.

A compound of formula (a) wherein A is phenyl, pyridyl, and the like can be prepared as described in EP 747 355 and as described by Naito, R. et al., *Chem. Pharm. Bull.*, 1998, 46(8), 1286.

Scheme B

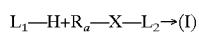

A compound of formula (I) wherein $L_1$ comprises a nitrogen that is bonded to X, can be prepared by alkylating a corresponding compound of formula $L_1$—H wherein —H is bound to the nitrogen, with a corresponding compound of $R_a$—X—$L_2$ wherein X and $L_2$ have any of the values defined herein and $R_a$ is a suitable leaving group. Suitable leaving groups an conditions for the alkylation of an amine are known in the art (for example, see Advanced Organic Chemistry, Reaction Mechanisms and Structure, 4 ed., 1992, Jerry March, John Wiley & Sons, New York. For example, $R_a$ can be halo (e.g. chloro, bromo, or iodo), methylsulfonyl, 4-tolylsulfonyl, mesyl, or trifluoromethylsulfonyl.

Accordingly, the invention provides a method for preparing a compound of formula (I) wherein $L_1$ comprises a nitrogen that is bonded to X, comprising alkylating a corresponding compound of formula $L_1$—H with a compound of $R_a$—X—$L_2$ wherein X and $L_2$ have any of the values defined herein and $R_a$ is a suitable leaving group.

The invention also provides a compound of formula $L_1$—H wherein $L_1$, has any of the values defined herein. The following compounds are preferred compounds of formula $L_1$—H:

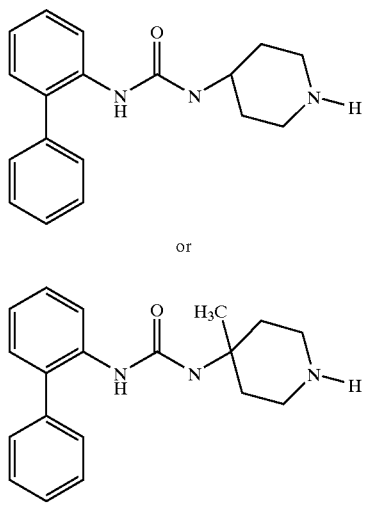

The invention also provides a compound of formula $R_a$—X—$L_2$ wherein X, and $L_2$ have any of the values defined herein and $R_a$ is a suitable leaving group. The compound of formula $L_1$—H can also be alkylated by treatment with an aldehyde of formula $L_2$—V—CHO (wherein —V—$CH_2$— is equivalent to —X—), under reductive alkylation conditions. Reagents and conditions suitable for carrying out the reductive alkylation of an amine are known in the art (for example, see Advanced Organic Chemistry, Reaction Mechanisms and Structure, 4 ed., 1992, Jerry March, John Wiley & Sons, New York).

Accordingly, the invention provides a method for preparing a compound of formula (I) wherein $L_1$ comprises a nitrogen that is bonded to X, comprising alkylating a corresponding compound of formula $L_1$—H with a compound of formula $L_2$—V—CHO (wherein —V—$CH_2$— has any of the values for —X— described herein).

Scheme C

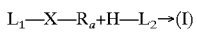

A compound of formula (I) wherein $L_2$ comprises a nitrogen that is bonded to X, can be prepared by alkylating a corresponding compound of formula $L_2$—H wherein —H is bound to the nitrogen, with a corresponding compound of $L_1$—X—$R_a$ wherein X and $L_1$ have any of the values defined herein and $R_a$ is a suitable leaving group. Suitable leaving groups an conditions for the alkylation of an amine are known in the art (for example, see Advanced Organic Chemistry, Reaction Mechanisms and Structure, 4 ed., 1992, Jerry March, John Wiley & Sons, New York. For example, $R_a$ can be halo (e.g. chloro, bromo, or iodo), methylsulfonyl, 4-tolylsulfonyl, mesyl, or trifluoromethylsulfonyl.

Accordingly, the invention provides a method for preparing a compound of formula (I) wherein $L_2$ comprises a nitrogen that is bonded to X, comprising alkylating a corresponding compound of formula $L_2$—H with a compound of $L_1$—X—$R_a$ wherein X and $L_1$ have any of the values defined herein and $R_a$ is a suitable leaving group.

The compound of formula $L_2$—H can also be alkylated by treatment with an aldehyde of formula $L_1$—V—CHO (wherein —V—$CH_2$— is equivalent to —X—), under reductive alkylation conditions. Reagents and conditions suitable for carrying out the reductive alkylation of an amine are known in the art (for example, see Advanced Organic Chemistry, Reaction Mechanisms and Structure, 4 ed., 1992, Jerry March, John Wiley & Sons, New York).

Accordingly, the invention provides a method for preparing a compound of formula (I) wherein $L_2$ comprises a nitrogen that is bonded to X, comprising alkylating a corresponding compound of formula $L_2$—H with a compound of formula $L_1$—V—CHO (wherein —V—$CH_2$— has any of the values for —X— described herein).

It will be understood that the alkylation reactions in Schemes B and C can optionally be carried out using suitably protected derivatives of $L_1$—H, $L_2$—H, $L_1$—X—$R_a$, $R_a$—X—$L_2$, $L_1$—V—CHO, and $L_2$—V—CHO. Suitable protecting groups as well as conditions for their incorporation and removal are known in the art (for example, see Greene, T. W.; Wutz, P. G. M. "Protecting Groups In Organic Synthesis" second edition, 1991, New York, John Wiley & sons, Inc.). Thus, a compound of formula (I) can also be prepared by deprotecting a corresponding compound of formula (I) bearing one or more protecting groups.

Accordingly, the invention provides a method for preparing a compound of formula (I) comprising deprotecting a corresponding compound of formula (I) that bears one or more protecting groups. The invention also provides an intermediate compound of formula (I) that bears one or more protecting groups.

Combinatorial Synthesis

Compounds of formula (I) can conveniently be prepared using combinatorial synthesis methods (e.g. solid phase and solution phase combinatorial synthesis methods) that are known in the art. For example, compounds of formula (I) can be prepared using combinatorial methods like those escribed in International Patent Application Publication Number WO 99/64043.

Utility, Testing, and Administration

Utility

The compounds of this invention are muscarinic receptor antagonists or agonists. A preferred sub-groug of compounds of the invention are $M_2$ muscarinic receptor antagonists. Accordingly, the compounds and pharmaceutical compositions of this invention are useful in the treatment and prevention of diseases mediated by these receptors such as chronic obstructive pulmonary disease, asthma, irritable bowel syndrome, urinary incontinence, rhinitis, spasmodic colitis, chronic cystitis, and Alzheimer's disease, senile dementia, glaucoma, schizophrenia, gastroesophageal reflux disease, cardiac arrhythmia, hyper salvation syndromes, and the like.

Testing

The ability of the compounds of formula (I) to inhibit a muscarinic receptor (e.g. the $M_2$ or $M_3$ subtype) may be demonstrated using a variety of in vitro assays and in vivo assays known in the field, or may be demonstrated using an assay described in biological examples 1–6 below.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, intravesicular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.001 to about 1 g, usually about 0.1 to about 500 mg, more usually about 1 to about 50 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of Formula (I) above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

EXAMPLES

The following preparations and examples are given to enable those skilled in the art to more clearly understand and to practice the present invention. They should not be considered as limiting the scope of the invention, but merely as being illustrative and representative thereof.

In the examples below, the following abbreviations have the following meanings. Unless otherwise stated, all temperatures are in degrees Celsius. If an abbreviation is not defined, it has its generally accepted meaning.

| | |
|---|---|
| g | gram |
| mg | milligram |
| min | minute |
| ml | milliliter |
| mmol | millimol |

Synthetic Examples

Example 1

The intermediate compound of formula 1B was prepared as follows.

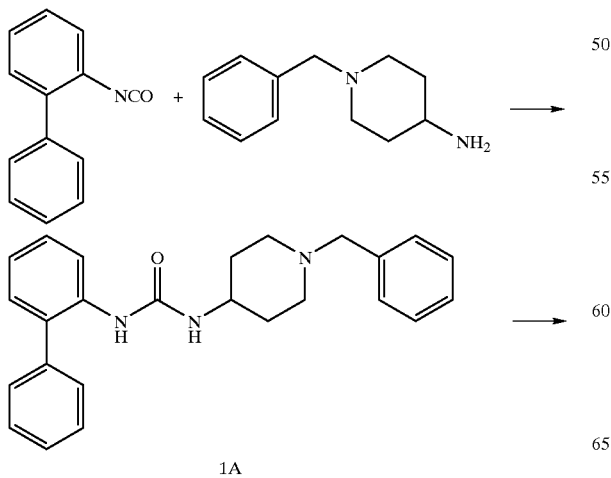

1A

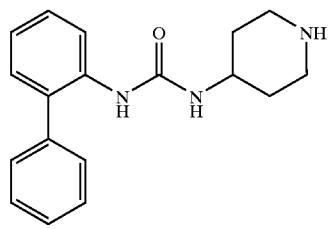

1B

Biphenyl-2-isocynate (50 g, 256 mmol) was dissolved in 400 mL anhydrous acetonitrile in a 2L rbf at room temperature. After cooling to 0 C. using an ice bath, a solution of 4-amino-N-benzylpiperidine (48.8 g, 256 mmol) dissolved in 400 mL anhydrous acetonitrile was added over 5 minutes. Precipitate was observed immediately. After 15 minutes, an additional 600 mL anhydrous acetonitrile was added to permit stirring of the viscous solution for 12 h at 35° C. The solids were filtered, and washed with cold acetonitrile then dried under vacuum, yielding a colorless solid (100 g, 98%). This material was characterized by $^1$H-NMR, $^{13}$C-NMR and MS.

Compound 1A (20 g, 52 mmol) was dissolved in 800 mL of a 3:1 mixture of anhydrous methanol to anhydrous DMF. Aqueous HCl was added (0.75 mL of 37% conc solution, 7.6 mmol) and nitrogen gas bubbled through the solution vigorously for 20 min. Pd(OH)2 (Pearlman's catalyst, 5 g) was added under a stream of nitrogen. A large balloon containing H2 gas was placed and the solution allowed to stir for 4d. The solution was passed twice through pads of celite to remove the catalyst, and the solution evaporated to dryness under vacuum to yield a colorless solid (13 g, 85%). This material was characterized by $^1$H-NMR, $^{13}$C-NMR and MS.

Following the procedures described above but substituting the appropriate starting materials, the compounds of the invention (formula (VI)) listed in Table A below were prepared. Unless otherwise noted, for the compounds in Tables A—F, $L_2$ is attached to X through the secondary non-aromatic amine of $L_2$.

TABLE A (VI)

| Compound | L2 | Mass Spec Found |
|---|---|---|
| 1 | A224 | 411.6 |
| 2 | A87 | 488.6 |
| 3 | A172 | 517.7 |
| 4 | A90 | 514.7 |
| 5 | A141 | 607.8 |
| 6 | A169 | 517.7 |
| 7 | A164 | 517.78 |
| 8 | A208 | 451.6 |
| 9 | A199 | 467.6 |
| 10 | A23 | 534.6 |
| 11 | A70 | 542.7 |
| 12 | A73 | 542.7 |

TABLE A-continued

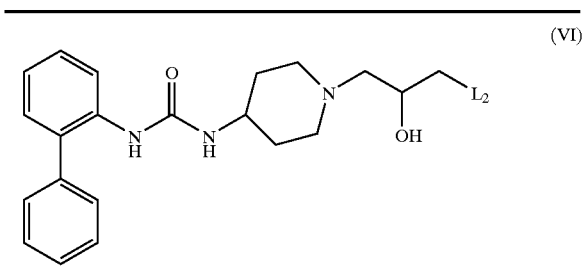

(VI)

| Compound | L2 | Mass Spec Found |
|---|---|---|
| 13 | A156 | 605.8 |
| 14 | A95 | 511.7 |
| 15 | A115 | 467.6 |
| 16 | A156 | 605.8 |
| 17 | A516 | 487.7 |
| 18 | A364 | 511.7 |
| 19 | A96 | 485.6 |
| 20 | A508 | 537.7 |
| 21 | A509 | 537.7 |
| 22 | A190 | 505.7 |
| 23 | (135) | 616.8 |
| 24 | A51 | 532.7 |
| 25 | A524 | 496.7 |
| 26 | A410 | 542.7 |
| 27 | A368 | 516.7 |
| 28 | A84 | 515.7 |
| 29 | A65 | 516.7 |
| 30 | A193 | 548.8 |
| 31 | A142 | 604.8 |
| 32 | A177 | 556.8 |
| 33 | A68 | 515.7 |
| 34 | A501 | 529.7 |
| 35 | A525 | 574.7 |
| 36 | A168 | 554.7 |
| 37 | A437 | 604.8 |
| 38 | A61 | 536.7 |
| 39 | A117 | 480.6 |
| 40 | A166 | 542.7 |
| 41 | 78 | 520.7 |
| 42 | A49 | 583.7 |
| 43 | A367 | 514.7 |
| 44 | A526 | 572.7 |
| 45 | A229 | 547.7 |
| 46 | A239 | 427.6 |
| 47 | A179 | 483.7 |
| 48 | A182 | 437.6 |
| 49 | A55 | 467.6 |
| 50 | A510 | 514.7 |
| 51 | A502 | 502.7 |
| 52 | A43 | 551.7 |
| 53 | A218 | 518.7 |
| 54 | A123 | 494.6 |
| 55 | A126 | 538.7 |
| 56 | A134 | 534.6 |
| 57 | A120 | 480.6 |
| 58 | A157 | 517.7 |
| 59 | A396 | 533.7 |
| 60 | A25 | 569.7 |
| 61 | A83 | 559.7 |
| 62 | A161 | 469.6 |
| 63 | A11* | 571.1 |
| 64 | A420 | 554.7 |
| 65 | A135 | 541.7 |
| 66 | A411 | 543.7 |
| 67 | A88 | 531.7 |
| 68 | A386 | 527.7 |
| 69 | A404 | 538.7 |
| 70 | A72 | 529.7 |
| 71 | A26 | 569.8 |
| 72 | A75 | 513.7 |
| 73 | A419 | 553.7 |
| 74 | A375 | 517.7 |
| 75 | A20 | 527.7 |
| 76 | A427 | 571.7 |

TABLE A-continued

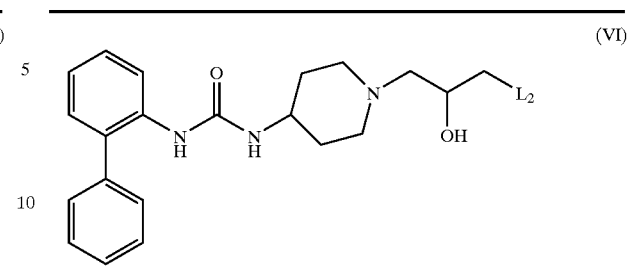

(VI)

| Compound | L2 | Mass Spec Found |
|---|---|---|
| 77 | A527 | 619.8 |
| 78 | A9 | 485.6 |
| 79 | A520 | 467.6 |
| 80 | A19 | 453.6 |
| 81 | A513 | 551.7 |
| 82 | A10 | 517.7 |
| 83 | A110 | 466.6 |
| 84 | A4 | 494.6 |
| 85 | A19 | 453.6 |
| 86 | A103 | 530.7 |
| 87 | A60 | 536.7 |
| 88 | A131 | 600.7 |
| 89 | A114 | 440.6 |
| 90 | A197 | 468.6 |
| 91 | A151 | 451.6 |
| 92 | A195 | 463.6 |
| 93 | A528 | 495.7 |
| 94 | A347 | 487.7 |
| 95 | A328 | 467.6 |
| 96 | A22 | 526.7 |
| 97 | A336 | 480.6 |
| 98 | A77 | 585.8 |
| 99 | A145 | 452.6 |
| 100 | A211 | 550.7 |

Following the procedures described above but substituting appropriate starting materials, the compounds of the invention (formula (VII)) listed in Table B below were prepared.

TABLE B

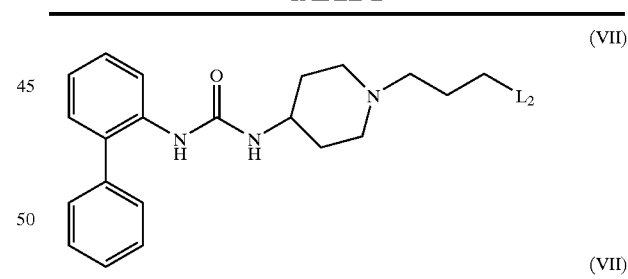

(VII)

| Compound | L2 | Mass Spec Found |
|---|---|---|
| 101 | A224 | 395.6 |
| 102 | A87 | 472.6 |
| 103 | A529 | 381.5 |
| 104 | A530 | 533.1 |
| 105 | A172 | 501.7 |
| 106 | A141 | 591.8 |
| 107 | A164 | 501.7 |
| 108 | A199 | 451.6 |
| 109 | A70 | 526.7 |
| 110 | A73 | 526.7 |
| 111 | A156 | 589.8 |
| 112 | A230 | 521.7 |
| 113 | A391 | 515.7 |
| 114 | A95 | 495.7 |
| 115 | A156 | 589.8 |

TABLE B-continued

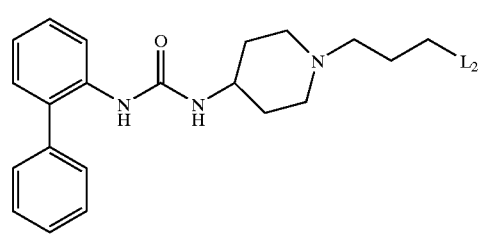

(VII)

| Compound | L2 | Mass Spec Found |
|---|---|---|
| 116 | A516 | 471.7 |
| 117 | A97 | 495.7 |
| 118 | A96 | 469.6 |
| 119 | A508 | 521.7 |
| 120 | A509 | 521.7 |
| 121 | A190 | 489.7 |
| 122 | A435 | 600.8 |
| 123 | A410 | 526.7 |
| 124 | A84 | 499.7 |
| 125 | A193 | 532.8 |
| 126 | A142 | 588.8 |
| 127 | A177 | 540.8 |
| 128 | A68 | 499.7 |
| 129 | A433 | 588.8 |
| 130 | A166 | 526.7 |
| 131 | A31 | 498.7 |
| 132 | A526 | 556.7 |
| 133 | A436 | 616.1 |
| 134 | A50 | 602.1 |
| 135 | A132 | 505.7 |
| 136 | A231 | 526.5 |
| 137 | A229 | 531.7 |
| 138 | A401 | 522.1 |
| 139 | A373 | 501.7 |
| 140 | A90 | 498.7 |
| 141 | A502 | 486.7 |
| 142 | A43 | 535.7 |
| 143 | A43@ | 536.7 |
| 144 | A576 | 522.7 |
| 145 | A374 | 501.7 |
| 146 | A17 | 511.7 |
| 147 | A21 | 517.7 |
| 148 | A83 | 543.7 |
| 149 | A531 | 538.7 |
| 150 | A125 | 525.7 |
| 151 | A210 | 527.7 |
| 152 | A88 | 515.7 |
| 153 | A78 | 511.7 |
| 154 | A404 | 522.7 |
| 155 | A72 | 513.7 |
| 156 | A26 | 553.8 |
| 157 | A75 | 497.7 |
| 158 | A419 | 537.7 |
| 159 | A527 | 603.8 |
| 160 | A520 | 451.6 |
| 161 | A513 | 535.7 |
| 162 | A164 | 501.7 |
| 163 | A4 | 478.7 |
| 164 | A521 | 515.7 |
| 165 | A60 | 520.7 |
| 166 | A522 | 584.7 |
| 167 | A192 | 551.7 |
| 168 | A122 | 533.7 |
| 169 | A109 | 499.7 |
| 170 | A383 | 507.7 |
| 171 | A395 | 516.7 |
| 172 | A503 | 594.8 |
| 173 | A528 | 479.7 |
| 174 | A99 | 471.7 |
| 175 | A22 | 510.7 |
| 176 | A532 | 569.8 |

Following the procedures described above but substituting appropriate starting materials, the compounds of the invention (formula (VIII)) listed in Table C below were prepared.

TABLE C

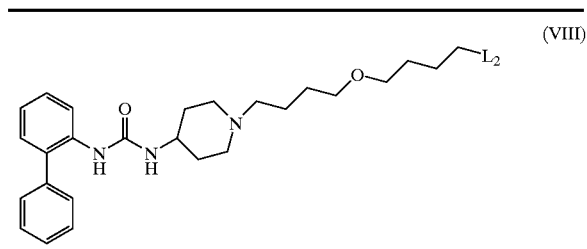

(VIII)

| Compound | L2 | Mass Spec Found |
|---|---|---|
| 177 | A508 | 607.8 |
| 178 | A509 | 607.8 |
| 179 | A501 | 599.8 |
| 180 | A90 | 584.8 |
| 181 | A502 | 572.8 |
| 182 | A43 | 621.8 |
| 183 | A513 | 621.8 |
| 184 | A503 | 681.0 |
| 185 | A87 | 558.8 |
| 186 | A164 | 587.8 |
| 187 | A90 | 584.8 |
| 188 | A90@ | 585.8 |
| 189 | A10 | 587.8 |
| 190 | A172 | 587.8 |
| 191 | A208 | 521.7 |
| 192 | A330 | 537.8 |
| 193 | A70 | 612.9 |
| 194 | A73 | 612.9 |
| 195 | A8 | 601.8 |
| 196 | A95 | 581.8 |
| 197 | A115 | 537.8 |
| 198 | A516 | 557.8 |
| 199 | A97 | 581.8 |
| 200 | A96 | 555.8 |
| 201 | A358 | 575.9 |
| 202 | A517 | 687.0 |
| 203 | A62 | 612.9 |
| 204 | A74 | 586.8 |
| 205 | A84 | 585.8 |
| 206 | A65 | 586.8 |
| 207 | A193 | 618.9 |
| 208 | A142 | 674.9 |
| 209 | A177 | 626.9 |
| 210 | A501 | 585.8 |
| 211 | A217 | 644.8 |
| 212 | A168 | 624.9 |
| 213 | A166 | 612.9 |
| 214 | A31 | 584.8 |
| 215 | A28 | 642.9 |
| 216 | A104 | 702.3 |
| 217 | A144 | 608.2 |
| 218 | A373 | 587.8 |
| 219 | A90@ | 585.8 |
| 220 | A43@ | 622.8 |
| 221 | A576 | 608.8 |
| 222 | A374 | 587.8 |
| 223 | A17 | 597.9 |
| 224 | A396 | 603.8 |
| 225 | A214 | 625.9 |
| 226 | A83 | 629.8 |
| 227 | A418 | 622.9 |
| 228 | A135 | 611.6 |
| 229 | A210 | 613.9 |
| 230 | A88 | 601.8 |
| 231 | A404 | 608.8 |
| 232 | A121 | 624.8 |
| 233 | A520 | 537.8 |
| 234 | A164 | 587.8 |
| 235 | A4 | 564.8 |
| 236 | A521 | 601.8 |
| 237 | A60 | 606.9 |
| 238 | A522 | 670.9 |

TABLE C-continued (VIII)

| Compound | L2 | Mass Spec Found |
|---|---|---|
| 239 | A109 | 585.8 |
| 240 | A22 | 596.8 |
| 241 | A532 | 655.9 |
| 242 | A397 | 604.7 |
| 243 | A120 | 550.8 |
| 244 | A533 | 509.7 |
| 245 | A505* | 626.9 |
| 246 | A506 | 598.8 |
| 247 | A431 | 659.9 |
| 248 | A388 | 597.9 |
| 249 | A366 | 583.8 |
| 250 | A534 | 578.8 |
| 251 | A417 | 622.9 |
| 252 | A577 | 575.8 |
| 253 | A319 | 536.7 |
| 254 | A381 | 593.8 |
| 255 | A338 | 550.8 |
| 256 | A329 | 537.8 |
| 257 | A403 | 608.8 |
| 258 | A333 | 549.8 |

Following the procedures described above but substituting appropriate starting materials, the compounds of the invention (formula (IX)) listed in Table D below were prepared.

TABLE D (IX)

| Compound | L2 | Mass Spec Found |
|---|---|---|
| 259 | A508 | 591.8 |
| 260 | A509 | 591.8 |
| 261 | A501 | 583.8 |
| 262 | A510 | 568.8 |
| 263 | A502 | 556.8 |
| 264 | A43 | 605.8 |
| 265 | A512 | 581.8 |
| 266 | A513 | 605.8 |
| 267 | A503 | 665.0 |
| 268 | A223 | 542.8 |
| 269 | A224 | 465.7 |
| 272 | A535 | 661.9 |
| 273 | A536 | 571.8 |
| 274 | A537 | 571.8 |
| 275 | A306 | 505.7 |
| 276 | A580 | 521.8 |
| 277 | A578 | 588.7 |
| 278 | A538 | 596.9 |
| 279 | A539 | 596.9 |
| 280 | A321 | 520.8 |

TABLE D-continued (IX)

| Compound | L2 | Mass Spec Found |
|---|---|---|
| 281 | A156 | 659.9 |
| 282 | A400 | 591.9 |
| 283 | A8 | 585.8 |
| 284 | A363 | 565.8 |
| 285 | A359 | 560.8 |
| 286 | A324 | 521.8 |
| 287 | A156 | 659.9 |
| 288 | A516 | 541.8 |
| 289 | A364 | 565.8 |
| 290 | A346 | 539.8 |
| 291 | A581 | 559.9 |
| 292 | A517 | 671.0 |
| 293 | A394 | 586.8 |
| 294 | A410 | 596.9 |
| 295 | A368 | 570.8 |
| 296 | A84 | 569.8 |
| 297 | A369 | 570.8 |
| 298 | A193 | 602.9 |
| 299 | A432 | 658.9 |
| 300 | A423 | 610.9 |
| 301 | A68 | 569.8 |
| 302 | A525 | 628.8 |
| 303 | A168 | 608.9 |
| 304 | A45 | 658.9 |
| 305 | A398 | 590.8 |
| 306 | A117 | 534.8 |
| 307 | A166 | 596.9 |
| 308 | A378 | 574.9 |
| 309 | A198 | 523.8 |
| 310 | A137 | 534.8 |
| 311 | A316 | 520.7 |
| 312 | A339 | 534.8 |
| 313 | A322 | 520.8 |
| 314 | A352 | 548.8 |
| 315 | A430 | 637.9 |
| 316 | A384 | 568.8 |
| 317 | A28 | 626.9 |
| 318 | A436 | 686.3 |
| 319 | A50 | 672.2 |
| 320 | A132 | 575.8 |
| 321 | A205 | 550.8 |
| 322 | A154 | 566.8 |
| 323 | A413 | 601.8 |
| 324 | A144 | 592.2 |
| 325 | A301 | 481.7 |
| 326 | A344 | 537.8 |
| 327 | A182 | 491.7 |
| 328 | A373 | 571.18 |
| 329 | A340 | 535.8 |
| 330 | A325 | 521.8 |
| 331 | A94 | 567.8 |
| 332 | A218 | 572.8 |
| 333 | A348 | 548.8 |
| 334 | A519 | 588.9 |
| 335 | A126 | 592.8 |
| 336 | A397 | 588.7 |
| 337 | A155 | 571.18 |
| 338 | A308 | 507.7 |
| 339 | A387 | 581.9 |
| 340 | A311 | 521.8 |
| 341 | A21 | 587.8 |
| 342 | A426 | 623.9 |
| 343 | A422 | 609.9 |
| 344 | A424 | 613.8 |

TABLE D-continued

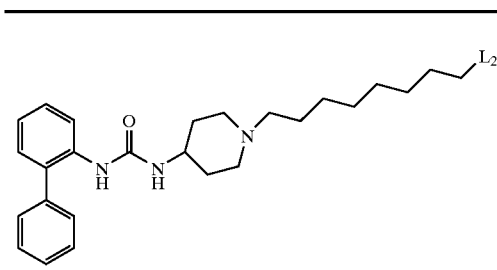

(IX)

| Compound | L2 | Mass Spec Found |
|---|---|---|
| 345 | A418 | 606.9 |
| 346 | A161 | 523.7 |
| 347 | A11 | 625.9 |
| 348 | A420 | 608.8 |
| 349 | A406 | 595.8 |
| 350 | A210 | 597.9 |
| 351 | A374 | 585.8 |
| 352 | A386 | 581.9 |
| 353 | A540 | 592.8 |
| 354 | A72 | 583.8 |
| 355 | A26 | 623.9 |
| 356 | A365 | 567.8 |
| 357 | A419 | 607.9 |
| 358 | A341 | 535.8 |
| 359 | A412 | 599.8 |
| 360 | A121 | 608.8 |
| 361 | A375 | 571.8 |
| 362 | A385 | 581.8 |
| 363 | A427 | 625.9 |
| 364 | A527 | 674.0 |
| 365 | A345 | 539.8 |
| 366 | A327 | 521.8 |
| 367 | A583 | 507.7 |
| 368 | A227 | 673.0 |
| 369 | A312 | 511.7 |
| 370 | A4115 | 603.8 |
| 371 | A376 | 571.8 |
| 372 | A98 | 592.8 |
| 373 | A317 | 520.7 |
| 374 | A4 | 548.8 |
| 375 | A165 | 535.7 |
| 376 | A380 | 577.8 |
| 377 | A541 | 585.8 |
| 378 | A584 | 589.8 |
| 379 | A311 | 507.7 |
| 380 | A521 | 585.8 |
| 381 | A390 | 584.9 |
| 382 | A399 | 590.9 |
| 383 | A131 | 654.9 |
| 384 | A27 | 495.7 |
| 385 | A204 | 548.8 |
| 386 | A122 | 603.9 |
| 387 | A350 | 548.8 |
| 388 | A425 | 617.9 |
| 389 | A109 | 569.8 |
| 390 | A542 | 664.0 |
| 391 | A114 | 494.7 |
| 392 | A331 | 522.7 |
| 393 | A235 | 577.8 |
| 394 | A543 | 586.8 |
| 395 | A151 | 505.8 |
| 396 | A313 | 517.7 |
| 397 | A528 | 549.9 |
| 398 | A99 | 541.8 |
| 399 | A328 | 521.8 |
| 400 | A384 | 580.8 |
| 401 | A314 | 519.8 |
| 402 | A335 | 534.8 |
| 403 | A360 | 562.2 |
| 404 | A77 | 639.9 |
| 405 | A145 | 506.7 |
| 406 | A71 | 563.8 |
| 407 | A124 | 523.7 |
| 408 | A377 | 573.8 |

TABLE D-continued

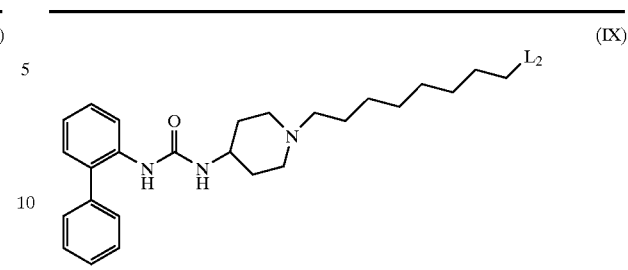

(IX)

| Compound | L2 | Mass Spec Found |
|---|---|---|
| 409 | A416 | 604.8 |
| 410 | A329 | 521.8 |
| 411 | A43 | 606.8 |
| 412 | A307 | 505.8 |
| 413 | A397 | 588.7 |
| 414 | A337# | 534.8 |
| 415 | A303 | 493.7 |
| 416 | A544 | 610.9 |
| 417 | A506 | 582.8 |
| 418 | A431 | 643.9 |
| 419 | A388 | 581.9 |
| 420 | A366 | 567.8 |
| 421 | A523 | 562.8 |
| 422 | A545 | 606.9 |
| 423 | A577 | 559.8 |
| 424 | A319 | 520.7 |
| 425 | A381 | 577.8 |
| 426 | A351 | 548.8 |
| 427 | A338 | 534.8 |
| 428 | A362 | 563.8 |
| 429 | A507 | 477.7 |
| 430 | A402 | 592.8 |
| 431 | A403 | 592.8 |
| 432 | A315 | 519.8 |
| 433 | A333 | 533.8 |

Following the procedures described above but substituting appropriate starting materials, the compounds of the invention (formula (X)) listed in Table E below were prepared.

TABLE E (X)

| Compound | L2 | Mass Spec Found |
|---|---|---|
| 434 | A130 | 525.7 |
| 435 | A105 | 521.8 |
| 436 | A356 | 571.8 |
| 437 | A415 | 617.8 |
| 438 | A579 | 585.8 |
| 439 | A98 | 606.8 |
| 440 | A317 | 534.8 |
| 441 | A349 | 562.8 |
| 442 | A465 | 549.8 |
| 443 | A380 | 591.8 |
| 444 | A546 | 599.8 |
| 445 | A547 | 548.8 |
| 446 | A548 | 587.8 |
| 447 | A386 | 676.9 |

TABLE E-continued
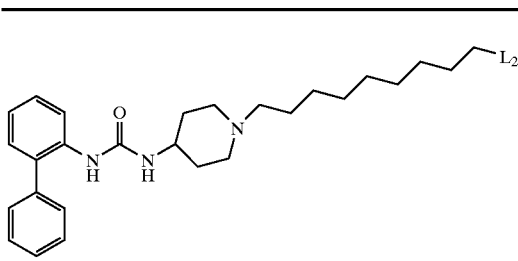
(X)
| Compound | L2 | Mass Spec Found |
|---|---|---|
| 448 | A311 | 521.8 |
| 449 | A521 | 599.9 |
| 450 | A127 | 490.7 |
| 451 | A390 | 598.9 |
| 452 | A399 | 604.9 |
| 453 | A342 | 550.8 |
| 454 | A27 | 509.7 |
| 455 | A549 | 562.9 |
| 456 | A550 | 635.9 |
| 457 | A238 | 617.9 |
| 458 | A350 | 562.8 |
| 459 | A425 | 631.9 |
| 460 | A109 | 583.9 |
| 461 | A114 | 508.7 |
| 462 | A331 | 536.8 |
| 463 | A551 | 585.8 |
| 464 | A235 | 591.9 |
| 465 | A395 | 600.8 |
| 466 | A13 | 615.8 |
| 467 | A552 | 507.8 |
| 468 | A151 | 519.8 |
| 469 | A313 | 531.8 |
| 470 | A35 | 507.8 |
| 471 | A99 | 555.8 |
| 472 | A328 | 535.8 |
| 473 | A22 | 594.9 |
| 474 | A314 | 533.8 |
| 475 | A336 | 548.8 |
| 476 | A228 | 684.0 |
| 477 | A360 | 576.2 |
| 478 | A145 | 520.7 |
| 479 | A302 | 505.8 |
| 480 | A71 | 577.8 |
| 481 | A553 | 656.9 |
| 482 | A124 | 537.8 |
| 483 | A554 | 587.8 |
| 484 | A416 | 618.9 |
| 485 | A555 | 625.9 |
| 486 | A556 | 701.0 |
| 487 | A557 | 716.0 |
| 488 | A558 | 638.9 |
| 489 | A559 | 624.8 |
| 490 | A560 | 654.0 |
| 491 | A561 | 654.0 |
| 492 | A508 | 605.8 |
| 493 | A509 | 605.8 |
| 494 | A501 | 597.9 |
| 495 | A510 | 582.8 |
| 496 | A502 | 570.8 |
| 497 | A43 | 619.9 |
| 498 | A512 | 595.8 |
| 499 | A513 | 619.9 |
| 500 | A503 | 679.0 |
| 501 | A504 | 556.8 |
| 502 | A514 | 613.9 |
| 503 | A402 | 606.9 |
| 504 | A403 | 606.9 |
| 505 | A397 | 602.8 |
| 506 | A337 | 548.8 |
| 507 | A303 | 507.7 |
| 508 | A505 | 624.9 |
| 509 | A506 | 596.9 |
| 510 | A431 | 658.0 |
| 511 | A388 | 595.9 |
TABLE E-continued
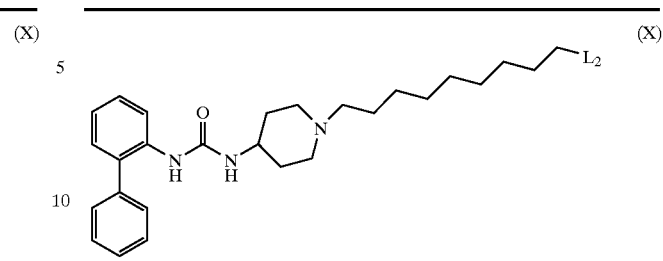
(X)
| Compound | L2 | Mass Spec Found |
|---|---|---|
| 512 | A366 | 581.9 |
| 513 | A523 | 576.8 |
| 514 | A417 | 620.9 |
| 515 | A577 | 573.8 |
| 516 | A319 | 534.8 |
| 517 | A381 | 591.8 |
| 518 | A351 | 562.8 |
| 519 | A338 | 548.8 |
| 520 | A362 | 577.8 |
| 521 | A507 | 491.7 |
| 522 | A324 | 535.8 |
| 523 | A315 | 533.8 |
| 524 | A333 | 547.8 |
| 525 | A427 | 718.8 |
| 526 | A402 | 685.8 |
| 527 | A562 | 506.7 |
| 528 | A563 | 506.7 |
| 529 | A564 | 520.8 |
| 530 | A565 | 731.0 |
| 531 | A370 | 585.8 |
| 532 | A371 | 585.8 |
| 533 | A372 | 585.8 |
| 534 | A587 | 519.7 |
| 535 | A330 | 535.8 |
| 536 | A320 | 534.8 |
| 537 | A578 | 602.8 |
| 538 | A588 | 548.8 |
| 539 | A538 | 610.9 |
| 540 | A539 | 610.9 |
| 541 | A321 | 534.8 |
| 542 | A156 | 674.0 |
| 543 | A141 | 675.9 |
| 544 | A569 | 687.0 |
| 545 | A400 | 605.9 |
| 546 | A391 | 599.9 |
| 547 | A363 | 579.8 |
| 548 | A359 | 574.9 |
| 549 | A311 | 535.8 |
| 550 | A570 | 602.9 |
| 551 | A515 | 674.0 |
| 552 | A178 | 680.0 |
| 553 | A364 | 579.8 |
| 554 | A346 | 553.8 |
| 555 | A358 | 573.9 |
| 556 | A517 | 685.0 |
| 557 | A571 | 634.0 |
| 558 | A51 | 600.8 |
| 559 | A64 | 564.8 |
| 560 | A67 | 619.9 |
| 561 | A62 | 610.9 |
| 562 | A180 | 617.9 |
| 563 | A74 | 584.8 |
| 564 | A84 | 583.8 |
| 565 | A65 | 584.8 |
| 566 | A193 | 616.9 |
| 567 | A432 | 672.9 |
| 568 | A200 | 591.9 |
| 569 | A177 | 624.9 |
| 570 | A572 | 632.0 |
| 571 | A174 | 603.9 |
| 572 | A68 | 583.8 |
| 573 | A525 | 642.9 |
| 574 | A168 | 622.9 |
| 575 | A45 | 673.0 |

TABLE E-continued

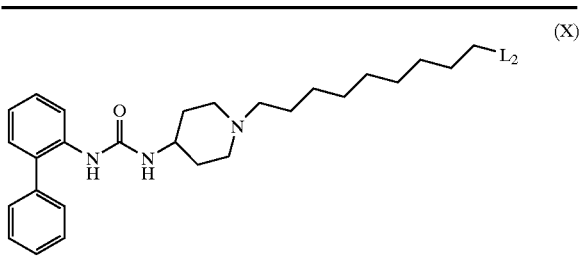

(X)

| Compound | L2 | Mass Spec Found |
|---|---|---|
| 576 | A61 | 604.8 |
| 577 | A117 | 548.8 |
| 578 | A166 | 610.9 |
| 579 | A378 | 588.9 |
| 580 | A137 | 548.8 |
| 581 | A34 | 534.8 |
| 582 | A93 | 548.8 |
| 583 | A59 | 562.9 |
| 584 | A585 | 651.9 |
| 585 | A31 | 582.8 |
| 586 | A28 | 640.9 |
| 587 | A436 | 700.3 |
| 588 | A50 | 686.3 |
| 589 | A3 | 675.0 |
| 590 | A379 | 589.8 |
| 591 | A573 | 610.7 |
| 592 | A355 | 564.8 |
| 593 | A413 | 615.9 |
| 594 | A401 | 606.3 |
| 595 | A301 | 495.7 |
| 596 | A179 | 551.8 |
| 597 | A82 | 551.8 |
| 598 | A12 | 585.8 |
| 599 | A55 | 535.8 |
| 600 | A133 | 607.9 |
| 601 | A94 | 581.8 |
| 602 | A100 | 570.8 |
| 603 | A123 | 562.8 |
| 604 | A589 | 606.9 |
| 605 | A134 | 602.8 |
| 606 | A203 | 548.8 |
| 607 | A17 | 595.9 |
| 608 | A66 | 535.8 |
| 609 | A214 | 623.9 |
| 610 | A574 | 627.9 |
| 611 | A154 | 585.8 |
| 612 | A6 | 636.9 |
| 613 | A185 | 521.8 |
| 614 | A2 | 525.7 |
| 615 | A119 | 569.8 |
| 616 | A21 | 601.8 |
| 617 | A25 | 637.9 |
| 618 | A33 | 620.9 |
| 619 | A161 | 537.8 |
| 620 | A11* | 639.9 |
| 621 | A420 | 622.9 |
| 622 | A135 | 609.9 |
| 623 | A210 | 611.9 |
| 624 | A88 | 599.9 |
| 625 | A72 | 597.9 |
| 626 | A69 | 521.8 |
| 627 | A26 | 637.9 |
| 628 | A365 | 581.9 |
| 629 | A171 | 621.9 |
| 630 | A81 | 549.8 |
| 631 | A412 | 613.9 |
| 632 | A121 | 622.9 |
| 633 | A18 | 663.9 |
| 634 | A232 | 585.8 |
| 635 | A575 | 670.0 |
| 636 | A20 | 595.8 |
| 637 | A153 | 639.9 |
| 638 | A590 | 688.0 |
| 639 | A91 | 477.7 |

TABLE E-continued

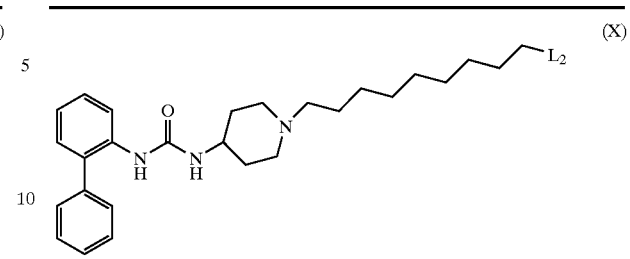

(X)

| Compound | L2 | Mass Spec Found |
|---|---|---|
| 640 | A9 | 553.8 |
| 641 | A194 | 535.8 |
| 642 | A310 | 521.8 |
| 643 | A227 | 687.0 |

Following the procedures described above but substituting appropriate starting materials, the compounds of the invention (formula (XI)) listed in Table F below were prepared.

TABLE F (XI)

| Compound | L2 | Mass Spec Found |
|---|---|---|
| 270 | A224 | 609.6 |
| 271 | A87 | 686.7 |

In the above tables *signifies that $L_2$ is attached to X through the piperidine nitrogen of $L_2$; @signifies that $L_2$ is attached to X through the pyridine nitrogen of $L_2$; and #signifies that $L_2$ is attached to X through the pyrrolidine nitrogen of $L_2$.

Formulation Examples

Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Example 2

A tablet Formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Example 8

A formulation may be prepared as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Example 9

A formulation may be prepared as follows:

| Ingredient | Quantity |
| --- | --- |
| Active Ingredient | 5.0 mg |
| Corn Oil | 1.0 mL |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Other suitable formulations for use in the present invention can be found in *Remington's Pharmaceutical Sciences*, edited by E. W. Martin (Mack Publishing Company, 18th ed., 1990).

Biological Examples

Example 1

$M_2$ Muscarinic Receptor In Vitro Binding Assay

The $M_2$ muscarininc receptor binding activity of compounds of the invention was tested as follows.

SF9 cell membranes containing human $M_2$ muscarinic receptor was obtained from NEN (Boston, Mass.). In 96-well microtiter plates, eight serial five-fold dilutions were prepared with the compound to be assayed; the highest concentration was typically 4 $\mu$M (4× the final concentration). To 100 $\mu$l of compound dilution was added 150 $\mu$L $M_3$ receptor membrane preparation in PBS/1.0 mM $MgCl_2$/pH 7.4. 50 $\mu$l of 3.2 nM 3H-N-methylscopolamine radioligand was added. The total volume in each well was then 300 $\mu$l. The filter plate was pre-blocked using 0.3% PEI for at least 15 minutes, and then washed twice with 200 $\mu$l PBS. The assay plate was incubated for 1 hour at room temperature with gentle shaking. The contents of the assay plate were then transferred to the filter plate, and washed three times using 200 $\mu$l PBS. About 40 $\mu$l of scint was added to each well and then the plate was allowed to sit at room temperature for 2 h, and then counted using a Packard Topcount NXT. Counting was typically performed for 1 minute per well using a standard protocol on a Packard top counter. The raw data was fit to a standard 4-parameter equation given below and a value of $IC_{50}$ obtained.

$Y=(a-d)/(1+(x/c)^b)+d$ where

| | | |
| --- | --- | --- |
| Y = cpm | a = total binding | b = slope |
| c = $IC_{50}$ | x = [compound] | d = nonspecific binding |

Representative compounds of the invention were found to have $pK_b$ values of greater than 6, and to have $IC_{50}$ values of less than about 50 $\mu$m.

A similar protocol was used to measure M1, M3, M4 and M5 human muscarinic receptor activity.

Example 2

Rat Heart Muscarinic Receptor in vitro Binding Assay

Tissue (rat heart) muscarininc receptor binding activity of compounds of the invention was tested as follows.

Muscarinic receptor enriched membranes were isolated from whole hearts (Pelfreeze Laboratories). Rat heart tissue was typically prepared as follows. 25 $\mu$l of ice cold buffer (20 mM HEPES, 100 mM NaCl/10 mM $MgCl_2$ at pH 7.5 with "Complete" protease inhibitor cocktail purchased from Boehringer Mannheim was added into an oakridge tube. To the tube was then added 2 g of rat heart (purchased from Harlan). The contents of the tube were then transferred to a wheaton glass cylinder and homogenized using a Polytron homogenizer (setting 22, 15 seconds×2), and then transferred back to the oakridge tube, and centrifuged for 10 minutes at 1500 g. The supernatant was removed and then centrifuged for 20 minutes at 45000 g. The supernatant was removed and the pellet resuspended in 5 mL buffer and transferred to a wheaton glass cylinder. This material was then homogenized using a Potter type glass teflon homogenizer with 7–8 passes. The material was then transferred to an oakridge tube and the total volume was brought up to 25 mL. This material was then centrifuged for 20 minutes at 45000 g, and the pellet re-suspended in 2 mL buffer using 2 passes of a teflon homogenizer, and stored at −80° C. until used.

A protocol similar to that used for cloned receptor binding was used: Eight serial five-fold dilutions were prepared with the compound to be assayed; the highest concentration was typically 4 $\mu$M (4× the final concentration). To 50 $\mu$l of compound dilution in a 96-well assay plate was added an appropriate amount of rat heart membrane (usually 12.5 $\mu$l of membrane prep in 87.5 $\mu$l of 20 mM HEPES, 100 mM NaCl/10 mM $MgCl_2$ at pH 7.5). The amount of membrane added depends in general on the results of signal optimization, and ranges from 6.25–12.5 $\mu$l. Last, 50 $\mu$l of 2.12 nM 3H-N-methylscopolamine radioligand was added. The total volume in each well was 200 $\mu$l. The filter plate was pre-blocked using 0.3% PEI for at least 15 min., and then washed twice with 200 $\mu$l PBS. The assay plate was incubated for 1 h at room temperature with gentle shaking. The contents of the assay plate were then transferred to the filter plate, and washed three times using 200 $\mu$l PBS. About 40 $\mu$l of scint was added to each well and then the plate was allowed to sit at room temperature for 18 h, and then counted using a Packard Topcount NXT. Counting was typically performed for 1 min., per well using a standard protocol on the Packard counter. The data was fit to normal isotherms and values for inhibition constants were extracted. Representative compounds of the invention were found to have $pK_b$ values of greater than 6, and to have $IC_{50}$ values of less than about 50 μm.

A similar procedure was used to measure muscarinic receptor binding at rat submaxillary gland, rat bladder, rat submandibular gland, guinea pig heart, guinea pig submaxillary gland, guinea pig bladder, and guinea pig submandibular gland, as well as in similar human tissues.

Example 3

Rat Bladder $M_3$ in vitro Binding Assay

Bladder was comprised of both $M_2$ and $M_3$ muscarinic receptors. The ratio was typically 4:1 $M_2$:$M_3$. In order to measure binding of test compounds to one of $M_2$ or $M_3$, the other was blocked with a reversible ligand that binds selectively to that receptor. The following example illustrates the procedure for $M_3$ bladder binding.

Membranes from rat bladder were prepared in a similar fashion to that used to isolate heart membrane above. Eight serial five-fold dilutions were prepared with the compound to be assayed in compound dilution buffer (20 mM HEPES/ 100 mM NaCl/10 mM $MgCl_2$/4 μM Methoctramine); the highest concentration was typically 4 μM (4× the final concentration). The concentration of methoctramine was sufficient to block >99% of the $M_2$ receptor in bladder, but less than 40% of the $M_3$ receptor in bladder. To 50 μl of compound dilution in a 96-well assay plate was added an appropriate amount of rat heart membrane (usually 25 μl of membrane prep in 75 μl of 20 mM HEPES, 100 mM NaCl/10 mM $MgCl_2$ at pH 7.5). The amount of membrane added depended in general on the results of signal optimization, and ranged from 12.5–25. Last, 50 μl of 2.12 nM 3H-N-methylscopolamine radioligand in compound dilution buffer was added. The total volume in each well was 200 μl. The final concentration of methoctramine was 2 μM. The filter plate was pre-blocked using 0.3% PEI for at least 15 mins., and then washed twice with 200 μl PBS. The assay plate was incubated for 1 hour at room temperature with gentle shaking. The contents of the assay plate was then transferred to the filter plate, and washed three times using 200 μl PBS. About 40 μl of scint was added to each well, the plate was allowed to sit at room temperature for 18h, and then counted using a Packard Topcount NXT. Counting was typically performed for 1 minute per well using a standard protocol on the Packard counter. The data was fit to normal isotherms and values for inhibition constants were extracted. Representative compounds of the invention were found to have $IC_{50}$ values of less than about 500 μm.

A similar procedure was used to measure binding at bladder $M_2$, but in this case, 2 μM Darifenacin was used to block >99% of the $M_2$ receptor, but minimal $M_3$ receptor.

Example 4

Ex Vivo Rat Bladder Contraction Assay

The ability of the test compound to inhibit cholinergically stimulated bladder contraction was tested as follows.

Male Sprague-Dawley rats weighing 250–300 g are killed by $CO_2$ overdose. The bladder was removed and placed in a petri dish containing Krebs-Henseleit solution at room temperature. The apex and dome areas of the bladder were discarded and the remaining tissue cut into longitudinal strips (4 from each rat). The strips were mounted in an organ bath containing Krebs-Henseleit solution at 37° C., under a resting tension of 0.5 g. The tissues were allowed to equilibrate for 60 min., (washes at 0, 30 and 60 min.). Tension was readjusted to 1 g as necessary. A cumulative concentration response curve to carbachol (10–8 M to 10–5 M (e.g.) in 3-fold increments) was constructed in each tissue. Tissues were then washed every 5 min., for 30 min., and tension readjusted to 1 g. After additional 30 min., muscarinic antagonist (typically 1×10–7 M) or vehicle was added. Thirty minutes after antagonist or vehicle addition, a cumulative concentration response curve to carbachol (10–8M to 10–3M (e.g.)) was constructed. Data from each concentration response curve was expressed as a percentage of the maximum contraction to carbachol. The $EC_{50}$ values were calculated. The concentration-ratios were calculated taking into account any spontaneous shift in the control tissue. For competitive antagonists, the pKb value was calculated using the following equation:

$$pKB = -\frac{\log[\text{antagonist concentration}]}{CR-1}$$

Representative compounds of the invention were found to have $pK_b$ values of greater than 5.

Example 5

In vivo Rat Salivation Assay

Male Sprague-Dawley rats weighing 250–300 g were anesthetized with pentobarbital (60 mg/kg i.p.). Rats were placed on a heated blanket under a 20 degree incline. A swab was placed in the rat's mouth. Muscarinic antagonist or vehicle was administered i.v. via the tail vein. After 5 min., oxotremorine (0.3 mg/kg) was administered s.c. The swab was discarded and replaced by a pre-weighed swab. Saliva was then collected for 15 min. After 15 min., the swab was weighed and the difference in its weight was used to calculate the antisecretory potency of the antagonists. The data was fit to normal isotherms and $ID_{50}$ values were extracted.

Example 6

In vivo Bladder Assay

Male Sprague-Dawley rats weighing 250–300 g were anesthetized with urethane (1.3 g/kg, i.p.), inactin (25 mg/kg, i.p.), and xylazine (4 mg, i.p.). The jugular (or femoral) vein was isolated and ligated and a small incision was made in the vein distal to the ligation. A catheter (micro-Renathane tubing (0.014 mm ID×0.033 mm OD) filled with saline was inserted into the vein and secured into place with suture thread. The trachea was isolated and placed in a small hole between two of the rings. Tubing (1.57 mm ID×2.08 mm OD) was inserted into the trachea and tied into place with suture thread. The incision was closed leaving the tubing exposed. The tracheotomy was to prevent the animal from asphyxiating on his own saliva following oxotremorine administration. The stomach was shaved and then cleaned with ethanol. A midline sagital incision was made in the skin and muscle layers of the lower stomach. The bladder was exposed and the saline filled cannula (22-gauge needle attached to a pressure transducer with PE 90 tubing) was inserted into the apex of the bladder to the most distal part of the bladder. The bladder was placed back into the peritoneal cavity. The bladder was emptied manually by disconnecting the cannula and allowing the contents to flow out until the bladder was approximately 1 cm in diameter. The incision was closed with suture thread, first the muscle layer, then the skin in order to keep the bladder moist and warm. The exposed portion of the cannula to the skin surface was sutured to hold it in place. After 15 min. oxotremorine (0.3 mg/kg, SC, baseweight) was injected. After 10 min., (or until baseline stabilized) a test compound or a reference standard was injected with a dose equivalent to 0.005–0.01 mg/kg, IV, baseweight of atropine that produced a 30–70% decrease in intraluminal pressure. After 5 min., a high dose of atropine 0.1 mg/kg was injected, i.v., to establish the true 100% inhibition point.

For data analysis, the oxotremorine response (zero inhibition) was determined by measuring the mean pressure 1 minute prior to the antagonist injection. Then, to assess antagonist inhibition, mean pressure was mesured beginning at 1 minute and ending 2 minutes after antagonist administration. If the pressure had not leveled off after 1 minute, a wait was initiated until it was stable and then a 1-minute sample of the mean was taken. Lastly, to determine the true 100% inhibition point, the mean pressure was measured beginning 1 minutes and ending 2 minutes after the high dose atropine challenge. The percent inhibition by the antagonist can be determined by the ratio of the decrease from the zero to 100% values.

The formula is: oxotremorine mean–treatment mean *100 oxotremorine mean–atropine mean.

Additionally, the activity of a compound of the invention on other tissues can be determined using screening protocols that are known in the art. For example, an assessment of increased locomotor activity (assay for CNS penetration) can be carried out as described by Sipos M L, et al., (1999) *Psychopharmacology* 147(3):250–256; an assessment of the effects of a compound on gastrointestinal motility can be carried out as described by Macht D I, and Barba-Gose J (1931) *J Am Pharm Assoc* 20:558–564; an assessment of the effects of a compound on pupil diameter (mydriasis) can be carried out as described by Parry M, Heathcote B V (1982) *Life Sci* 31:1465–1471; and an assessment of a compounds effects on urinary bladder in dog can be carried out as described by Newgreen D T, et al. (1996) *J Urol* 155:600A.

Preferred compounds of the invention may display selectivity for one or more tissues over other tissues. For example, compounds of the invention that are useful for treating urinary incontinence may show higher activity in the assay of Example 6 than in the assay of Example 5.

Preferred compounds useful for treating urinary incontinence and irritable bowel syndrome have greater antagonist activity at the $M_2$ receptor than at the $M_3$ receptor or the other muscarinic receptors.

Preferred compounds useful for treating unwanted salivation have greater antagonist activity at the $M_3$ receptor than at the $M_2$ receptor or the other muscarinic receptors.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:
1. A compound of formula (IVa):

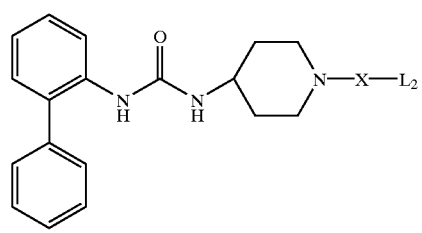

(IVa)

wherein:
X is a group of formula:

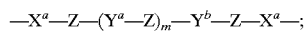

m is an integer of from 0 to 20;

$X^a$ at each separate occurrence is selected from the group consisting of —O—, —S—, —NR—, —C(O)—, —C(O)O—, —C(O)NR—, —C(S)—, —C(S)O—, —C(S)NR— or a covalent bond;

Z at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;

$Y^a$ and $Y^b$ at each separate occurrence are selected from the group consisting of —O—, —C(O)—, —OC(O)—, —C(O)O—, —NR—, —S(O)n-, —C(O)NR'—, —NR' C(O)—, —NR' C(O)NR'—, —NR' C(S)NR'—, —C(=NR')—NR'—, —NR'—C(=NR')—, —OC (O)—NR'—, —NR'—C(O)—O—, —N=C($X^a$)—NR'—, —NR'—C($X^a$)=N—, —P(O)(OR')—O—, —O—P(O)(OR')—, —S(O)$_n$CR' R"—, —S(O)$_n$—NR'—, —NR'—S(O)$_n$—, —S—S—, and a covalent bond;

n is 0, 1 or 2;

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

$L_2$ is a group of formula (d) or (e):

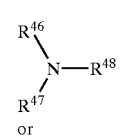

(d)

or

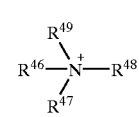

(e)

$R^{46}$ is alkyl, substituted alkyl, cycloalkyl, substituted cycloalkyl, or heterocycle;

$R^{47}$ is alkyl, substituted alkyl, aryl, acyl, heterocycle, or —COOR$^{50}$ where $R^{50}$ is alkyl; or $R^{46}$ and $R^{47}$ together with the nitrogen atom to which they are attached form heterocycle, which heterocycle can also optionally be substituted with one or more alkyl, substituted alkyl, alkenyl, substituted alkenyl, alkynyl, or substituted alkynyl;

$R^{48}$ is a covalent bond that attaches $L_2$ to X and $R^{49}$ is alkyl;

provided at least one of $X^a$, $Y^a$, $Y^b$ or Z is not a covalent bond;

or a pharmaceutically acceptable salt thereof.

2. The compound of claim 1 wherein $L_2$ is a group of the formula (d) and $R^{46}$ is alkyl or substituted alkyl; $R^{47}$ is alkyl, substituted alkyl, or heterocycle; or $R^{46}$ and $R^{47}$ together with the nitrogen atom to which they are attached form heterocycle.

3. The compound of claim 1 wherein $L_2$ is a group of formula (d) wherein $R^{46}$ and $R^{47}$ together with the nitrogen atom to which they are attached form heterocycle which is substituted with 1 to 5 substituents independently selected from the, group consisting of substituted alkyl, alkenyl, substituted alkenyl, alkynyl, and substituted alkynyl.

4. The compound of claim 1 wherein $L_2$ is a group of the formula (d) and $R^{46}$ and $R^{47}$ together with the nitrogen atom to which they are attached form a piperidine or pyrrolidine ring which ring is optionally substituted with 1 to 3 substituents independently selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, cyano, halogen, hydroxyl, keto, thioketo, carboxylalkyl, thioaryloxy, thioheteroaryloxy, thioheterocyclooxy, thiol, thioalkoxy, substituted thioalkoxy, heterocyclic, heterocyclooxy, hydroxyamino, alkoxyamino, alkyl, substituted alkyl, alkenyl, substituted alkenyl, alkynyl, and substituted alkynyl.

5. The compound of claim 1 wherein $L_2$ has any one of the formula A1-A590 shown hereinabove.

6. The compound of claim 1 wherein $L_2$ is A234, A363, A364, A153, A28, A324, A329, A562, A87, or A239.

7. The compound of claim 1, wherein X is alkylene optionally substituted with one, two, or three hydroxy groups, alkylene wherein one, two or three carbon atoms have been replaced by an oxygen atom, or -alkylene-phenylene-alkylene- wherein the phenylene ring is optionally substituted with one or two chloro or fluoro groups.

8. The compound of claim 1 wherein X is an alkylene group having from 3 to 20 carbon atoms; wherein one or more carbon atoms in the alkylene group is optionally replaced with —O—; and wherein the chain is optionally substituted on carbon with one or more hydroxyl.

9. The compound of claim 1 wherein X is nonane-1,9-diyl, octane-1,8-diyl, propane-1,3-diyl, 2-hydroxypropane-1,3-diyl, or 5-oxa-nonane-1,9-diyl.

10. The compound of claim 1 wherein X has the formula:

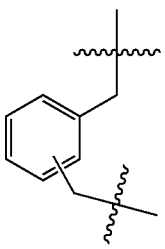

wherein the phenyl ring is optionally substituted with 1, 2, or 3 fluoro groups.

11. The compound of claim 1 wherein X has one of the following formula:

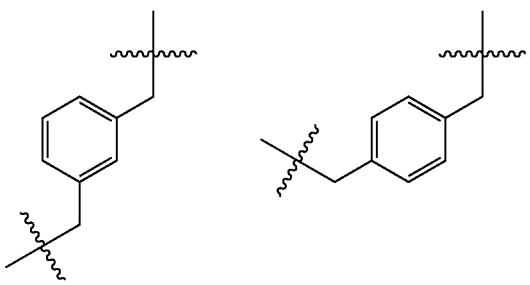

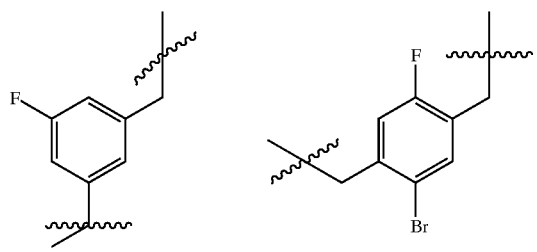

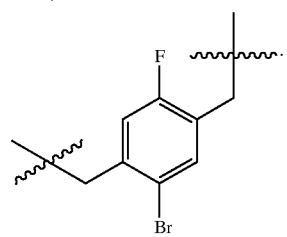

12. Compound number 1-643 as described in Table A, Table B, Table C, Table D, Table E, or Table F; or a pharmaceutically acceptable salt thereof.

13. A pharmaceutical composition comprising a pharmaceutically acceptable carrier and a compound of claim 11.

* * * * *